(12) United States Patent
Ishiguro et al.

(10) Patent No.: US 7,094,227 B2
(45) Date of Patent: Aug. 22, 2006

(54) DISPOSABLE DIAPER HAVING LEG FLAP ABSORBENT ARTICLES

(75) Inventors: Kenji Ishiguro, Tochigi (JP); Hidekazu Ito, Tochigi (JP); Takao Koyama, Tochigi (JP)

(73) Assignee: Kao Corporation, Tokyo (JP)

( * ) Notice: Subject to any disclaimer, the term of this patent is extended or adjusted under 35 U.S.C. 154(b) by 321 days.

(21) Appl. No.: 10/624,550

(22) Filed: Jul. 23, 2003

(65) Prior Publication Data

US 2004/0133181 A1 Jul. 8, 2004

(30) Foreign Application Priority Data

| Jul. 23, 2002 | (JP) | ............................. 2002-213734 |
| Jul. 23, 2002 | (JP) | ............................. 2002-213751 |
| Jul. 23, 2002 | (JP) | ............................. 2002-213763 |
| Jun. 11, 2003 | (JP) | ............................. 2003-166475 |

(51) Int. Cl.
*A61F 13/15* (2006.01)
*A61F 13/20* (2006.01)

(52) U.S. Cl. ........................... 604/385.25; 604/385.201

(58) Field of Classification Search .......... 604/385.01, 604/385.24, 385.25, 385.26, 385.27, 385.28, 604/385.201

See application file for complete search history.

(56) References Cited

U.S. PATENT DOCUMENTS

| 3,848,595 | A | * | 11/1974 | Endres | ................. | 604/385.201 |
| 5,382,246 | A | | 1/1995 | Kawano | | |
| 5,540,672 | A | * | 7/1996 | Roessler et al. | ........ | 604/385.26 |
| 5,779,690 | A | * | 7/1998 | Gustafsson et al. | .... | 604/385.09 |
| 5,957,907 | A | * | 9/1999 | Sauer | ..................... | 604/385.24 |
| 6,306,122 | B1 | * | 10/2001 | Narawa et al. | .......... | 604/385.3 |
| 6,309,487 | B1 | | 10/2001 | Herrin et al. | | |
| 6,369,291 | B1 | * | 4/2002 | Uchimoto et al. | ........... | 604/367 |
| 6,478,786 | B1 | * | 11/2002 | Glaug et al. | ............ | 604/385.27 |
| 6,562,015 | B1 | * | 5/2003 | Wilson | ................... | 604/385.01 |
| 6,767,343 | B1 | * | 7/2004 | Shimada et al. | ........ | 604/385.25 |
| 2002/0045879 | A1 | | 4/2002 | Karami | | |
| 2002/0049421 | A1 | * | 4/2002 | Hayase et al. | .......... | 604/385.27 |
| 2003/0078556 | A1 | * | 4/2003 | Sasaki et al. | ........... | 604/385.25 |
| 2004/0068246 | A1 | * | 4/2004 | Rose et al. | ............. | 604/385.27 |

(Continued)

FOREIGN PATENT DOCUMENTS

EP        0873738 A2   10/1998

(Continued)

OTHER PUBLICATIONS

English language translation of JP-3-121069-A (May 23, 1991).

(Continued)

*Primary Examiner*—Tatyana Zalukaeva
*Assistant Examiner*—Michael G. Bogart
(74) *Attorney, Agent, or Firm*—Birch, Stewart, Kolasch & Birch, LLP

(57) ABSTRACT

The present invention has a configuration such that a plurality of leg portion elastic members are arranged around the respective leg openings of a disposable diaper so that the respective leg portion elastic members are not connected or cross each other in a crotch portion, the minimum width of an absorbent article body at the crotch portion is within the range of from 250 to 350 mm, and the opposite side edges in the width direction of the absorbent article body in the crotch portion bend towards the external surface of the diaper, when worn. As a result, the ability for absorbing a large amount of body waste can be easily ensured, and the performance of preventing leakage from the crotch portion can be easily improved.

14 Claims, 22 Drawing Sheets

U.S. PATENT DOCUMENTS

| | | | |
|---|---|---|---|
| 2004/0133180 A1* | 7/2004 | Mori et al. | 604/385.25 |
| 2005/0004544 A1* | 1/2005 | Otsubo et al. | 604/385.01 |
| 2005/0004548 A1* | 1/2005 | Otsubo et al. | 604/385.25 |
| 2005/0075618 A1* | 4/2005 | Kenmochi et al. | 604/385.27 |
| 2005/0096624 A1* | 5/2005 | Hoshino et al. | 604/385.27 |

FOREIGN PATENT DOCUMENTS

| | | |
|---|---|---|
| EP | 1174103 A2 | 1/2002 |
| EP | 1208827 A1 | 5/2002 |
| EP | 1219273 A2 | 7/2002 |

OTHER PUBLICATIONS

English language translation of JP-4-242643-A (Aug. 31, 1992).
English language translation of JP-4-67427-A (Jun. 15, 1992).
English language translation of JP-2002-200115-A (Jul. 16, 2002).

* cited by examiner (A)

(B)

(A)

(B)

DISPOSABLE DIAPER HAVING LEG FLAP ABSORBENT ARTICLES

FIELD OF THE INVENTION

The present invention relates to a disposable diaper.

BACKGROUND OF THE INVENTION

In the field of disposable diapers, preventing leakage of body waste is one important problem, while improvement in a wearer's comfort of the disposable diaper is another important problem. The comfortableness of the disposable diaper can be improved by narrowing the width of an area (crotch portion) where the diaper is applied to the crotch of a wearer while wearing, but if the width of the crotch portion is narrowed, the width of the absorbent article at the crotch portion is also narrowed. Since the absorption of the diaper is determined by the volume of the absorbent article, in a diaper in which the width of the absorbent article at the crotch portion is not sufficient, the absorption is insufficient, and leakage is likely to occur.

For example, in Japanese Patent Publication No. 5-33630, there is described a disposable diaper, in which an absorbent article is formed of a central absorbing portion having a width suitable for the crotch of a wearer, and outside absorbing portions provided outside thereof in the width direction, thereby the adhesion of the absorbent article to the crotch and the inner parts of the thighs is improved, while maintaining high absorption of the absorbent article, thereby improving the prevention of leakage. At the time of wearing this disposable diaper, the outside absorbing portions abut against the inner parts of the thighs of the wearer.

In this disposable diaper, however, since it is difficult to make the outside absorbing portions adhere to the inner parts of the thighs of the wearer sufficiently, leakage may occur via a gap formed between the outside absorbing portion and the inner part of the thigh.

In Japanese Patent No. 3242532, there is described a disposable diaper in which a first elastic member which can extend from the front of the thigh of one lower limb of the wearer through the crotch to the front of the thigh of the other lower limb, and a second elastic member which can extend from the back of the thigh of one lower limb of the wearer through the crotch to the back of the thigh of the other lower limb are arranged so that the first elastic member and the second elastic member cross each other in the crotch portion, and a third elastic member crossing the first elastic member and the second elastic member is arranged outside of the absorbent article in the crotch width direction, thereby enhancing the adhesion of the absorbent article around the legs of the wearer.

At the time of wearing this disposable diaper, the absorbent article is substantially divided into two kinds of portions, that is, a central absorbing portion applied to the crotch of the wearer and the outside absorbing portions applied to the inner parts of the thighs, by the first elastic member and the second elastic member.

In Japanese Patent Publication No. 11-1010007, there is described a disposable diaper ("pull-on" type paper diaper) in which the width of the outer layer sheet defining the external shape of the diaper is less than the width of the absorbent article at least in the crotch region, and an elastically flexible portion for fastening the right and left leg portions is provided from the front section to the back section respectively in the right and left leg portions.

In the disposable diapers described in the above patent publication, however, when the body waste absorbed by the outside absorbing portions moves towards the central absorbing portion, the first elastic member and the second elastic member may be obstructive and stagnate movement, and hence, there is still room for improvement both in its absorbing performance and amount absorbed. Similarly, in the disposable diaper ("pull-on" type paper diaper) disclosed in the above Patent Publication, since the elastically flexible portion is provided from the front section to the back section respectively in the right and left leg portions, the elastically flexible portion may become obstructive and stagnate the movement of the body waste, and hence, there is still room for improvement both in its absorbing performance and amount absorbed.

SUMMARY OF THE INVENTION

The present invention relates to a disposable diaper having a liquid-holding type absorbent article body in which an absorbent article is arranged between a liquid permeable top sheet and a liquid impermeable back sheet, in which a pair of right and left leg openings through which the legs pass at least at the time of wearing the disposable diaper is formed, and a plurality of leg portion elastic members is arranged around the respective leg openings in an extended state, wherein the leg portion elastic member includes at least one first leg portion elastic member provided in the front side portion applied to the abdomen of a wearer so as to draw an arc along the leg openings, and at least one second leg portion elastic member provided in the back side portion applied to the back of the wearer so as to draw an arc along the leg openings, and isolated from the first leg portion elastic members in the crotch portion applied to the crotch of the wearer when worn, the minimum width of the absorbent article body at the crotch portion is within the range of from about 250 to 350 mm, and the opposite side edges in the width direction of the absorbent article body in the crotch portion bend towards the external surface when worn, so that the respective side edges in the width direction serve as leg flap absorbent articles which abut against the inner part of the thigh of the wearer.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

Figure 1:
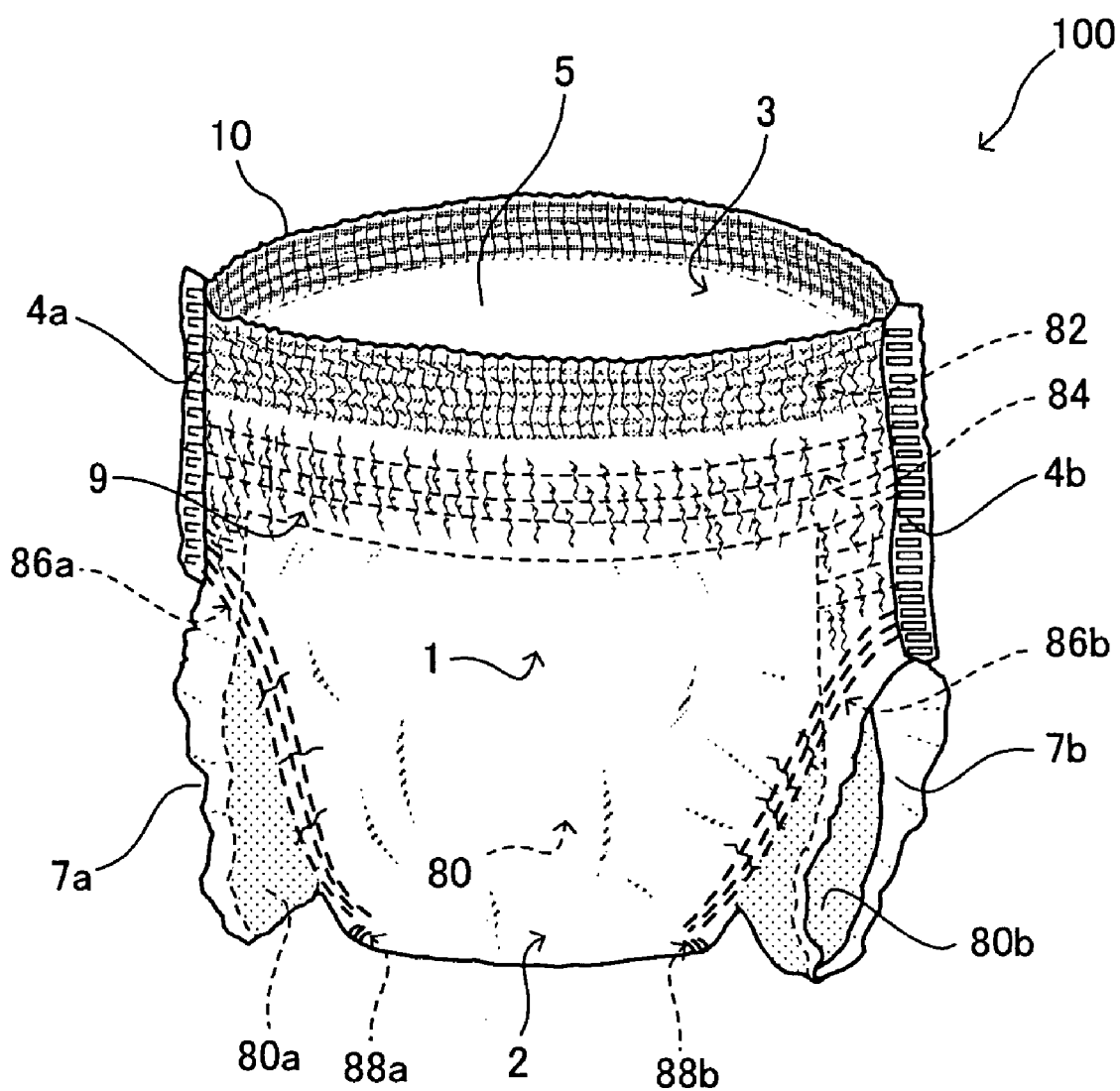
FIG. 1 is a perspective view schematically showing the state when a pull-on type disposable diaper in a first embodiment according to the present invention is worn.

All publications cited herein are hereby incorporated by reference.

The present invention relates to a disposable diaper, which makes it easy to ensure absorption sufficient for absorbing a large amount of body waste, and has improved performance of preventing leakage from the crotch portion.

In the disposable diaper of the present invention, since the minimum width of the absorbent article body in the crotch portion is within the range of from about 250 to 350 mm, absorption sufficient for absorbing a large amount of body waste can be ensured. In preferred embodiments, for further increasing the absorbing performance of the absorbent article body, it is preferred that the minimum width be within the range of from 270 mm to 310 mm.

At the time of wearing a disposable diaper of an embodiment of the present invention, the opposite side edges in the width direction of the absorbent article body in the crotch portion preferably bend toward the external surface (back sheet side), and the respective side edges in the width direction preferably serve as leg flap absorbent articles which abut against the inner parts of the thighs of the wearer. Therefore, the body waste exuded from the crotch portion can be absorbed by the leg flap absorbent articles. As a result, such disposable diaper can easily prevent leakage from the crotch portion.

As used herein, the term "width" refers to the width of the body in the disposable diaper. In the description of the disposable diaper of the present invention, dimensions of various portions are specifically mentioned, but these dimensions are the dimensions when a pull-on type disposable diaper is expanded and held in a strained state with regard to the pull-on type disposable diaper, and dimensions when an expanding type disposable diaper is held in a strained state with regard to the expanding type disposable diaper. As used herein, the term "pull-on type disposable diaper is expanded and held in a strained state" refers to the state when the front side portion and the back side portion of the pull-on type disposable diaper are peeled off at junctions formed on the right and left opposite sides of the diaper, and the diaper is held in the state that a tension is applied in the width direction and in a direction orthogonal to the width direction as seen from a plan view, so that the deformation of the outer layer sheet due to the shrinkage of the elastic member provided in the diaper substantially disappears.

The term "expanding type disposable diaper is held in a strained state" refer to a state when the diaper is held so that a tension is applied in the width direction and a direction orthogonal to the width direction as seen in plan view, so that the deformation of the outer layer sheet due to the shrinkage of the elastic member provided in the diaper substantially disappears.

The terms "first leg portion elastic member" and "second leg portion elastic member" used in the disposable diaper of the present invention respectively refer to the elastic member or an area in the elastic member, arranged as described above in a state with the extending stress manifested, and an elastic member or an area where the extending stress has disappeared or the extended state has been released is not included in such definition term.

Various embodiments and modified examples of the disposable diaper of the present invention will be specifically described below.

FIRST EMBODIMENT

FIG. 1 schematically shows pull-on type disposable diaper in a first embodiment in the worn state. A disposable diaper 100 shown here is a pull-on type disposable diaper (hereinafter referred to as "pull-on type disposable diaper 100"), and the pull-on type disposable diaper 100 has an outer layer sheet 10 which defines the external shape of the diaper, and an absorbent article body 80 fixed on the inner surface of the outer layer sheet 10.

The outer layer sheet 10 can be divided into a front side portion 1 applied to the abdomen, a crotch portion 2 applied to the crotch, and a back side portion 3 applied to the back of a wearer. The front side portion 1 and the back side portion 3 are joined with each other at the right and left opposite side edges in the width direction, by a method such as heat sealing, high-frequency sealing or ultrasonic sealing, to form junctions 4a and 4b. As a result, the outer layer sheet 10 is formed in a pants shape having a waist opening 5 through which the body of a wearer passes, and a pair of right and left leg openings 7a and 7b through which the legs of the wearer pass (in FIG. 1, only one leg opening 7b is shown).

The outer layer sheet 10 can be formed, for example, by a single sheet, or by joining a plurality of sheets in the thickness direction. It is also possible to overlap another sheet, as necessary, outside of the outer layer sheet 10. The outer layer sheet 10 in this embodiment is obtained by joining two sheets in the thickness direction, as described later.

The absorbent article body 80 has a structure such that an absorbent article is arranged between a liquid permeable top sheet and a liquid impermeable back sheet, as described below, and the absorbent article body 80 is arranged on the inner surface of the outer layer sheet 10 (on the face located on the wearer's side when worn), from the front side portion 1 to the crotch portion 2, and to the back side portion 3.

In order to improve the fit to the wearer's waist, a plurality of waist elastic members 82 are arranged in a ring shape over the whole periphery of the waist, around the waist opening 5, to form waist gathers. In order to improve the fit around the body of the wearer, a plurality of girth elastic members 84 are arranged in a ring shape over the whole periphery of the girth, below the area where the waist elastic members 82 are arranged (girth portion 9), to form girth gathers. The girth portion 9 refers to the portion located below the position where the waist elastic members 82 are arranged, and above the leg openings 7a and 7b, as shown in FIG. 1, in the state with the waist opening 5 directed upward.

In order to improve the fit of the area from the groin to the inner parts of the thighs of the wearer, a plurality of first leg portion elastic members 86a and a plurality of second leg portion elastic members 88a are arranged around the leg opening 7a, and a plurality of first leg portion elastic members 86b and a plurality of second leg portion elastic members 88b are arranged around the leg opening 7b, respectively, to form leg gathers.

The respective first leg portion elastic members 86a and 86b are provided so as to draw an arc along the leg opening 7a or 7b from the front side portion 1 to the crotch portion 2, and the second leg portion elastic members 88a and 88b are provided so as to draw an arc along the leg opening 7a or 7b from the back side portion 3 to the crotch portion 2.

The first leg portion elastic member 86a arranged on the leg opening 7a side and the first leg portion elastic member 86b arranged on the leg opening 7b side are isolated from each other, and the second leg portion elastic member 88a arranged on the leg opening 7a side and the second leg portion elastic member 88b arranged on the leg opening 7b side are also isolated from each other.

Similarly, the first leg portion elastic member 86a and the second leg portion elastic member 88a arranged on the leg opening 7a side are isolated from each other, and the first leg portion elastic member 86b and the second leg portion elastic member 88b arranged on the leg opening 7b side are also isolated from each other.

At the time of wearing the pull-on type disposable diaper 100, the opposite side edges in the width direction of the absorbent article body 80 in the crotch portion 2 bend towards the external surface of the diaper, so that the respective side edges in the width direction serve as leg flap absorbent articles 80a, 80b, which abut against the inner parts of the thighs of the wearer. Bending of the absorbent article body 80 at this time occurs substantially along the first leg portion elastic member 86a or 86b located outermost in the width direction, and along the second leg portion elastic member 88a or 88b located outermost in the width direction. In FIG. 1, for easy understanding of the position of the leg flap absorbent articles 80a and 80b, the main distribution area of these leg flap absorbent articles 80a and 80b are indicated by shading.

The structure of the pull-on type disposable diaper 100 will be described in detail, with reference to FIG. 2 and FIG. 3.

Figure 2:
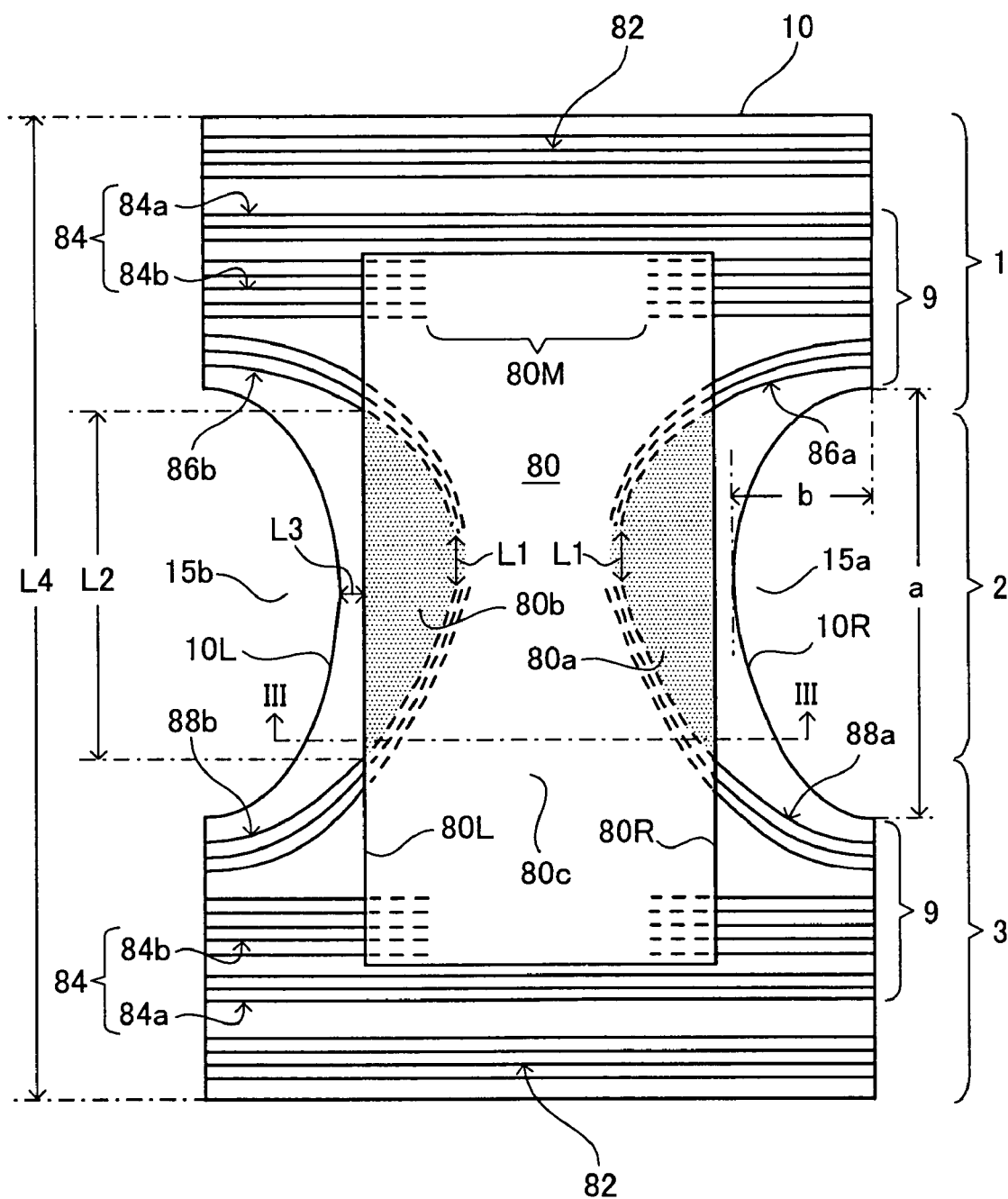
FIG. 2 is a plan view schematically showing the state when the pull-on type disposable diaper shown in FIG. 1 is expanded and held in a strained state, and is seen from the side which contacts with the skin of a wearer.

FIG. 2 schematically shows the state when the pull-on type disposable diaper 100 shown in FIG. 1 is expanded and held in a strained state, and is seen from the side which contacts with the skin of a wearer. FIG. 3 schematically shows a section of the pull-on type disposable diaper 100 along the line III—III shown in FIG. 2.

As shown in FIG. 2, the outer layer sheet 10 has a shape such that sinuses 15a and 15b are formed for forming the leg openings 7a and 7b, in the central portion of the right and left long sides of a sheet having a rectangular shape as seen in plan view. This outer layer sheet 10 is, as shown in FIG. 3, formed of an outer sheet 11, being the external surface of the pull-on type disposable diaper 100, and an inner sheet 12 joined on one face of the outer sheet 11.

The absorbent article body 80 has a rectangular shape as seen in plan view, for example as shown in FIG. 2, and is joined on the inner surface of the outer layer sheet 10 (on the surface located on the wearer's side when worn), so that the longitudinal direction thereof substantially agrees with the longitudinal direction of the outer layer sheet 10. The minimum width of the absorbent article body 80 in the crotch portion 2 is selected within the range of from about 250 mm to 350 mm.

Figure 3:
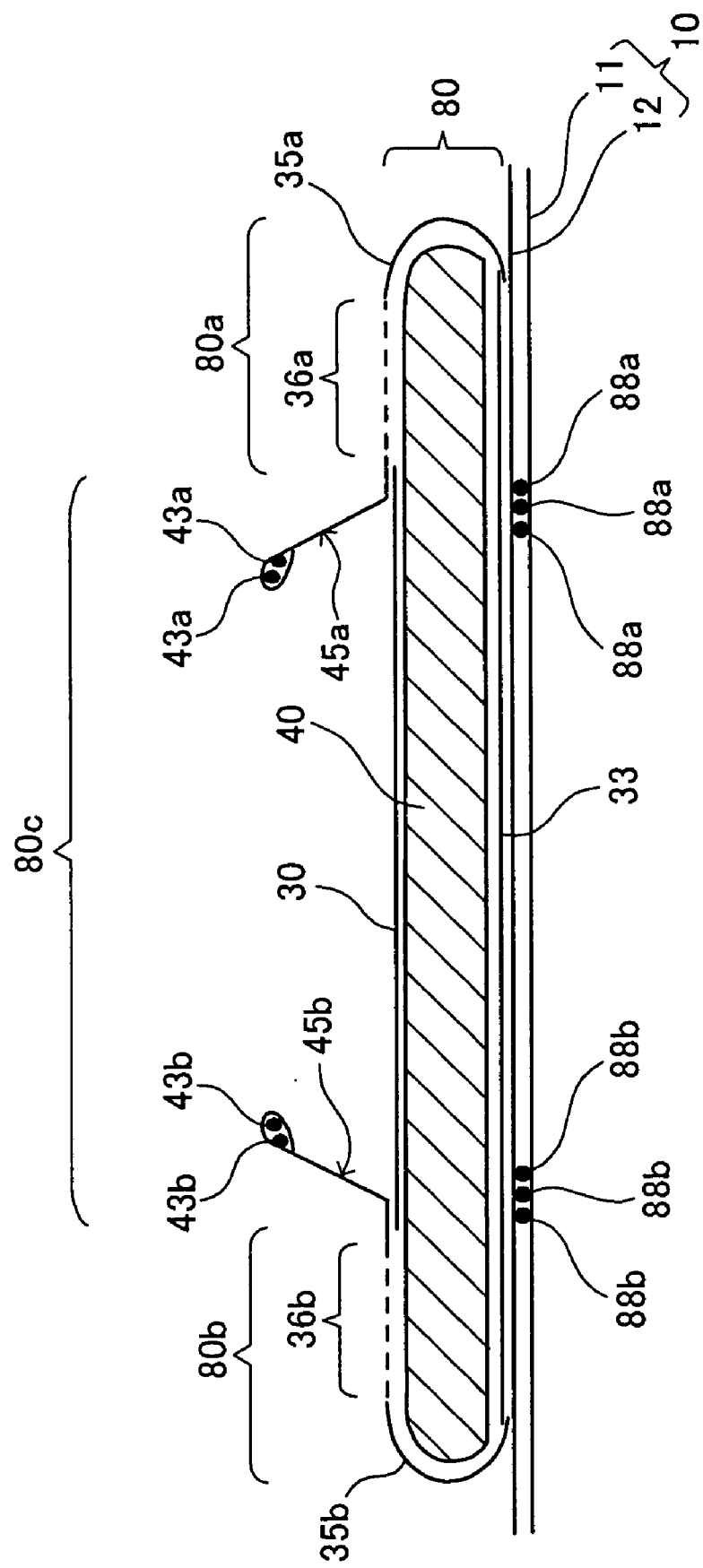
FIG. 3 is a schematic diagram of a section along the line III—III shown in FIG. 2.

As shown in FIG. 3, the absorbent article body 80 has a liquid permeable top sheet 30, a liquid impermeable back sheet 33, and an absorbent core 40 arranged therebetween. The top sheet 30 and the back sheet 33 are formed in a bag shape, together with liquid impermeable side edge sheets 35a and 35b provided on the opposite sides in the width direction, and the absorbent article 40 is arranged therein.

As described above, at the time of wearing the pull-on type disposable diaper 100, the opposite side edges in the width direction of the absorbent article body 80 bend towards the external surface of the diaper, respectively along the first leg portion elastic member 86a, 86b respectively located outermost in the width direction, and the second leg portion elastic member 88a, 88b respectively located outermost in the width direction, to form the leg flap absorbent articles 80a and 80b. In FIG. 2, shading is added in the areas, which become the leg flap absorbent articles 80a and 80b, of the absorbent article body 80. The area other than these areas, which become the leg flap absorbent articles 80a and 80b, of the absorbent article body 80 is referred to as a "central absorbent article 80c".

In order to absorb the body waste by the respective leg flap absorbent articles 80a and 80b, as shown in FIG. 3, liquid permeable side absorbing areas 36a and 36b are formed in the side edge sheets 35a and 35b on the upper face of the side flap absorbent articles 80a and 80b. These side absorbing areas 36a and 36b are for enabling the body waste which has flowed over beyond the first three-dimensional guards 45a and 45b, described later, to penetrate into the side flap absorbent articles 80a and 80b, and are formed by making a predetermined portion of the liquid impermeable side edge sheets 35a and 35b liquid permeable. Any method may be used without any particular limitation for making it liquid permeable, so long as the permeability of body waste can be improved as compared to the liquid impermeable area. Specifically, hydrophilic processing using a surfactant and a method of providing openings at predetermined portions of the side edge sheets 35a and 35b are several examples.

Though not shown for convenience sake in FIG. 2, in FIG. 3, a pair of first three-dimensional guards 45a and 45b are arranged on the top sheet 30, and on the right and left in the width direction of the top sheet 30.

As used herein, the term "three-dimensional guards" refers to a sheet for suppressing the permeation of body waste which is formed by raising the sheet so it is higher with respect to the circumference thereof at the time of wearing the disposable diaper, and the raised portion helps prevents the body waste from moving beyond the guards.

The illustrated first three-dimensional guards 45a and 45b have a structure such that the width of the side edge sheets 35a and 35b is wide, the area overlapping on the side edge in the width direction of the top sheet 30 is fixed to the side edge in the width direction of the top sheet 30 to designate this portion as a fixed end of the first three-dimensional guards, and a preferred number of elastic members 43a and 43b are arranged in an extended state on the free end side (the side edges on the top sheet 30 side) of the side edge sheets 35a and 35b. In FIG. 3, two elastic members 43a and 43b are respectively shown.

The first three-dimensional guards 45a and 45b are to stand up actually from the top sheet 30 at the time of wearing the disposable diaper 100, as illustrated, and in the state shown in FIG. 2, these guards are laid flat on the top sheet 30.

The respective waist elastic members 82, the respective girth elastic members 84, the respective first leg portion elastic members 86a and 86b, and the respective second leg portion elastic members 88a and 88b shown in FIG. 1 are fixed, as shown in FIG. 3, between the external sheet 11 and the internal sheet 12 by an adhesive. In FIG. 2, for convenience sake, the respective waist elastic members 82 are shown by a solid line, and for the respective girth elastic members 84, the respective first leg portion elastic members 86a and 86b, and the respective second leg portion elastic members 88a and 88b, the portions which do not overlap on the absorbent article body 80 as seen in plan view are indicated by solid lines, and the overlapped portions thereof are indicated by broken lines.

The number of the waist elastic members 82 shown in FIG. 2 is respectively four in the front side portion 1 and the back side portion 3, and the number of the girth elastic members 84 is respectively twelve in the front side portion 1 and the back side portion 3. Of the girth elastic members 84, the parts which do not overlap on the absorbent article body 80 as seen in plan view (four respectively in the front side portion 1 and the back side portion 3) are hereunder referred to as "first girth elastic members 84a", and the parts having the overlapped portions (four respectively in the right side and the left side of the front side portion 1and the back side portion 3) are hereunder referred to as "second girth elastic members 84b".

The respective first girth elastic members 84a are fixed in an extended state so as to form the elastic flexibility at least on the outer side in the width direction than the position of the right and left side edges 80R and 80L of the absorbent article body 80 (see FIG. 2). The respective second girth elastic members 84b are arranged so as not to form any elastic flexibility in the central part 80M in the width direction of the absorbent article body 80 in the state shown in FIG. 2. Specifically, the respective second girth elastic members 84b are arranged so as to avoid the central part 80M in the width direction, or otherwise arranged in a state such that the elastic flexibility is not existent or such extended state is released in the central part 80M in the width direction by utilizing a hot pressing process such as heat sealing or a cutting process.

The respective first leg portion elastic members 86a and 86b, and the respective second leg portion elastic members 88a and 88b are, as shown in FIG. 2, arranged around the sinus 15a or 15b formed on the outer layer sheet 10. By arranging the respective leg portion elastic members 86a, 86b, 88a and 88b as shown in FIG. 2, at the time of wearing the disposable diaper 100 (see FIG. 1), these leg portion elastic members 86a, 86b, 88a and 88b abut against the groin and the vicinity thereof of the wearer, to improve the fit from the groin to the thighs of the wearer.

In the pull-on type disposable diaper 100 embodiment having the above-described structure, the opposite side edges in the width direction of the absorbent article body 80 in the crotch portion 2 bend toward the external surface side (back sheet 33 side), thereby the respective side edges in the width direction serve as leg flap absorbent articles 80a and 80b which abut against the inner parts of the thighs of the wearer. As a result, the leg flap absorbent articles 80a and 80b can absorb the body waste which has leaked from the crotch portion 2.

In the pull-on type disposable diaper 100, since the respective first leg portion elastic members 86a and 86b, and the respective second leg portion elastic members 88a and 88b are isolated from each other in the crotch portion 2, a shift of the body waste from the respective leg flap absorbent articles 80a and 80b toward the central absorbent article 80c is likely to occur in the absorbent article body 80, as compared with the case where the first leg portion elastic members and the second leg portion elastic members cross each other in the crotch portion. As a result, the absorbing performance of the respective leg flap absorbent articles 80a and 80b is improved.

Moreover, in the pull-on type disposable diaper 100, the minimum width of the absorbent article body 80 in the crotch portion 2 is selected within the range of from about 250 mm to 350 mm. As a result, in the pull-on type disposable diaper 100, absorption sufficient for absorbing a large amount of body waste can be ensured.

Therefore, in the pull-on type disposable diaper 100, absorption sufficient for absorbing a large amount of body waste can be readily ensured, and the performance of preventing leakage from the crotch portion 2 can be readily improved.

In order to improve the fit of the pull-on type disposable diaper 100 around the legs and the crotch, particularly to the crotch, it is preferred that a gap ("a gap" as used herein refers to a gap in the longitudinal direction of the diaper) in the crotch portion between the first leg portion elastic members and the second leg portion elastic members, which is located on the same side in the width direction, that is, the gap L1 (see FIG. 2) between the first leg portion elastic members 86a and the second leg portion elastic members 88a, and the gap L1 (see FIG. 2) between the first leg portion elastic members 86b and the second leg portion elastic members 88b, be made within the range of from 1% to 70%, and more preferably, from 2% to 25% of the length L2 in the longitudinal direction of the corresponding leg flap absorbent article 80a or 80b (refers to a length defined by the respective leg portion elastic member located outermost in the width direction of the corresponding first and second leg portion elastic members. See FIG. 2).

Specifically, the gap L1 is preferably in the range of from 5 mm to 100 mm, and more preferably, from 10 mm to 50 mm. If the gap L1 is larger than the above range, the fit around the legs and the crotch of the wearer, particularly the fit to the crotch of the wearer, is not as proper, and a gap is likely to occur, thereby becoming difficult to prevent leakage from the crotch portion 2. On the other hand, if the gap L1 is narrower than the above range, the efficiency of the shift of the body waste from the leg flap absorbent articles 80a and 80b to the central absorbent article 80c decreases, and hence there is the possibility that the absorbing performance of the leg flap absorbent articles 80a and 80b decreases.

In the pull-on type disposable diaper 100, in order to make the minimum width of the absorbent article body 80 in the crotch portion 2 within the above-described range, the width of the outer layer sheet 10 in the crotch portion 2 is made wider. Specifically, by adjusting the respective shapes of the sinuses 15a and 15b (see FIG. 2) formed in the outer layer sheet 10, the width of the outer layer sheet 10 in the crotch portion 2 is made wider.

In other words, the shape of the respective sinuses 15a and 15b is selected such that, when the length in the longitudinal direction of the sinuses 15a and 15b is designated as "a" (see FIG. 2), and the maximum width (penetration depth) thereof is designated as "b" (see FIG. 2), a ratio of the length "a" in the longitudinal direction with respect to the maximum width "b", a/b is not smaller than about 3.3. By selecting the shape of the respective sinuses 15a and 15b in this manner, it becomes easy to make the shape of the leg openings 7a and 7b narrow in the width direction and wide in the longitudinal direction, without impairing the comfort to the wearer. As a result, it becomes easy to provide a wide absorbent article body 80, by increasing the width of the outer layer sheet 10 in the crotch portion 2.

From the standpoint of increasing the width of the absorbent article body 80 in the crotch portion 2, it is preferable to set the ratio a/b not smaller than 3.5. Moreover, the upper limit of the ratio a/b is preferably at most 7.0. The minimum width of the absorbent article body 80 is preferably within the range of from 270 mm to 310 mm, in order to improve the absorbing performance of the absorbent article body 80.

When arranging the absorbent article body 80 on the outer layer sheet 10, it is preferred to select the position of the absorbent article body 80 so that the shortest distance (for example, L3 shown in FIG. 2) from a point located innermost in the width direction at the side edges 10R and 10L (see FIG. 2) of the outer layer sheet 10 in the crotch portion 2 to the side edge 80R or 80L of the absorbent article body 80 closest to the point is at most 40 mm, and particularly, in the range of from 0 mm to 20 mm. By arranging the absorbent article body 80 in this manner, it becomes easy to ensure the width of the absorbent article body 80 in the crotch portion is sufficient.

Moreover, the maximum width of the respective leg flap absorbent articles 80a and 80b is preferably from about 20 mm to 100 mm, and more preferably, from 50 mm to 60 mm, when the first leg elastic members 86a and 86b and the second leg elastic members 88a and 88b are isolated from each other (e.g. when the leg elastic members do not exist in the central part in the width direction of the absorbent article), or from about 120 mm to 180 mm, and more preferably, from 130 mm to 160 mm, when the first leg elastic members 86a and 86b and the second leg elastic members 88a and 88b are respectively continuous (e.g. when the leg elastic members exist in the central part in the width direction of the absorbent article). If the maximum width of the respective leg flap absorbent articles 80a and 80b is within the above-described range, the absorption sufficient for preventing leakage from the crotch portion 2 can be easily ensured in the leg flap absorbent articles 80a and 80b.

Preferably, the length L2 in the longitudinal direction of the respective leg flap absorbent articles 80a and 80b is within the range of from about 1/5 to 2/3, more preferably, from 1/4 to 1/2, with respect to the length in the longitudinal direction of the diaper, specifically, with respect to L4 shown in FIG. 2. By setting the length L2 within the above range, the absorbent article body 80 easily bends in such a shape that the leg flap absorbent articles 80a and 80b abut against the inner parts of the thighs of the wearer with a sufficient length, when worn. As a result, a gap which forms between the leg flap absorbent articles 80a, 80b and the inner parts of the thighs of the wearer is closed, thereby improving the prevention of leakage from the crotch portion 2.

The pull-on type disposable diaper 100 having the above-described structure can be manufactured by various methods, so long as (i) the respective first leg portion elastic members 86a and 86b and the respective second leg portion elastic members 88a and 88b are isolated from each other, and these leg portion elastic members 86a, 86b, 88a and 88b are arranged so as to form the leg flap absorbent articles 80a and 80b; and (ii) the minimum width of the absorbent article body 80 in the crotch portion 2 is selected within the above-described range. Preferred materials that can be used for the production of the pull-on type disposable diaper 100 will be specifically described, while referring to reference symbols used in FIG. 2 or FIG. 3.

(1) Outer Sheet 10 and Internal Sheet 12

General nonwoven fabrics, for example, air-through nonwoven fabrics, heat rolled nonwoven fabrics, spunbonded nonwoven fabrics, spun lace nonwoven fabrics, meltblown nonwoven fabrics, and nonwoven fabrics obtained by using meltblowing and spunbonding processes (for example, SMS nonwoven fabric, SMMS nonwoven fabric and the like) can be used. Preferably, the outer sheet 10 and internal sheet 12 are water-repellent, taking prevention of leakage into consideration.

(2) Top Sheet 30

For example, woven fabrics formed of natural fibers, nonwoven fabrics formed of synthetic fibers, or open films comprising a thermoplastic resin may be used. It is preferred to use nonwoven fabrics formed of synthetic fibers, taking into consideration the feel at the time of being dry and wet, and the cost. The nonwoven fabrics formed of synthetic fibers include wet-type or dry-type synthetic fiber nonwoven fabrics used as a surface material of absorbent articles, more specifically, wet-type or dry-type nonwoven fabrics manufactured by using synthetic fibers such as polyethylene fiber, polypropylene fiber, polyester fiber, polyethylene-polypropylene bicomponent fiber polyethylene-polyester bicomponent fiber, polyvinyl alcohol fiber and rayon. It is preferred that the top sheet 30 be treated so as to be hydrophilic by for example, applying a surfactant, taking the absorptivity of body waste into consideration.

(3) Back Sheet 33

Liquid impermeable films made of a thermoplastic resin, used as a leak prevention sheet for absorbent articles, such as polyethylene film and polypropylene film can be used. Preferably, vapor permeable (moisture permeable) films obtained by mixing inorganic fine particles comprising calcium carbonate, titanium oxide and the like in the above-described thermoplastic resin, drawing and then forming such film, may be used.

(4) Side Edge Sheets 35a and 35b

For example, nonwoven fabrics formed by a wet process, dry process, spun lace process or spunbonding process can be used. Moreover, nonwoven fabrics directly formed by the meltblowing or spunbonding process can be used. For the material fibers for these nonwoven fabrics, mono-filament or bicomponent fiber formed of polyethylene (PE), polypropylene (PP), polyethylene terephthalate (PET) or the like can be used. For the bicomponent fibers, sheath-core bicomponent fibers, parallel type bicomponent fibers, or division type bicomponent fibers in which a fiber is divided into a plurality of fibers by heat or an external force can be used. Specific examples of the sheath-core bicomponent fibers include a polyolefin sheath-core bicomponent fiber in which the combination of the core component and the sheath component is PET/PE, PP/PE, or PET/PP (in either case, the former is the core component, and the latter is the sheath component). Among the nonwoven fabrics comprising a bicomponent fiber, a nonwoven fabric comprising a sheath-core bicomponent fiber in which a high elasticity resin is used for the core and a low elasticity and/or low melting point resin is used for the sheath has excellent feeling and elasticity, high productivity and safety, and low cost, and hence it is particularly preferable.

(5) Absorbent Core 40

A fiber assembly comprising, for example, a pulp fiber, cellulose fiber such as rayon, and a synthetic fiber such as polyethylene or polypropylene, and one in which a water absorptive polymer is contained in the whole or a part of the fiber assembly can be used.

(6) Respective Elastic Members

For the materials for forming the waist elastic members 82, the first girth elastic members 84a, the second girth elastic members 84b, the first leg portion elastic members 86a and 86b, and the second leg portion elastic members 88a and 88b, various elastic materials can be used, such as (a) synthetic rubbers such as styrene-butadiene rubber, butadiene rubber, isoprene rubber and neoprene rubber; (b) natural rubber; and (c) synthetic resins such as ethylene-vinyl acetate copolymer (EVA), flexible polyolefin, polyurethane and polyurethane foam. The form of the elastic members may be appropriately selected according to the application. However, for the waist elastic members 82 and the respective leg portion elastic members 86a, 86b, 88a and 88b, belt-shaped elastic members (flat rubber or the like) having a predetermined width are preferable, and for the first girth elastic members 84a and the second girth elastic members 84b, filamentous elastic members (filar rubber or the like) are preferable. Moreover, for the elastic members 43a and 43b for the first three-dimensional guards 45a and 45b, filamentous elastic members (filar rubber or the like), belt-shaped elastic members (flat rubber or the like) having a predetermined width, or thin-film elastic members (urethane film or the like) are preferable.

The respective elastic members are arranged at desired positions in an extended state, at the time of manufacturing the pull-on type disposable diaper 100. Therefore, when the pull-on type disposable diaper 100 is in a natural condition, the respective elastic members contract to some extent, to form gathers.

SECOND EMBODIMENT

Figure 4:
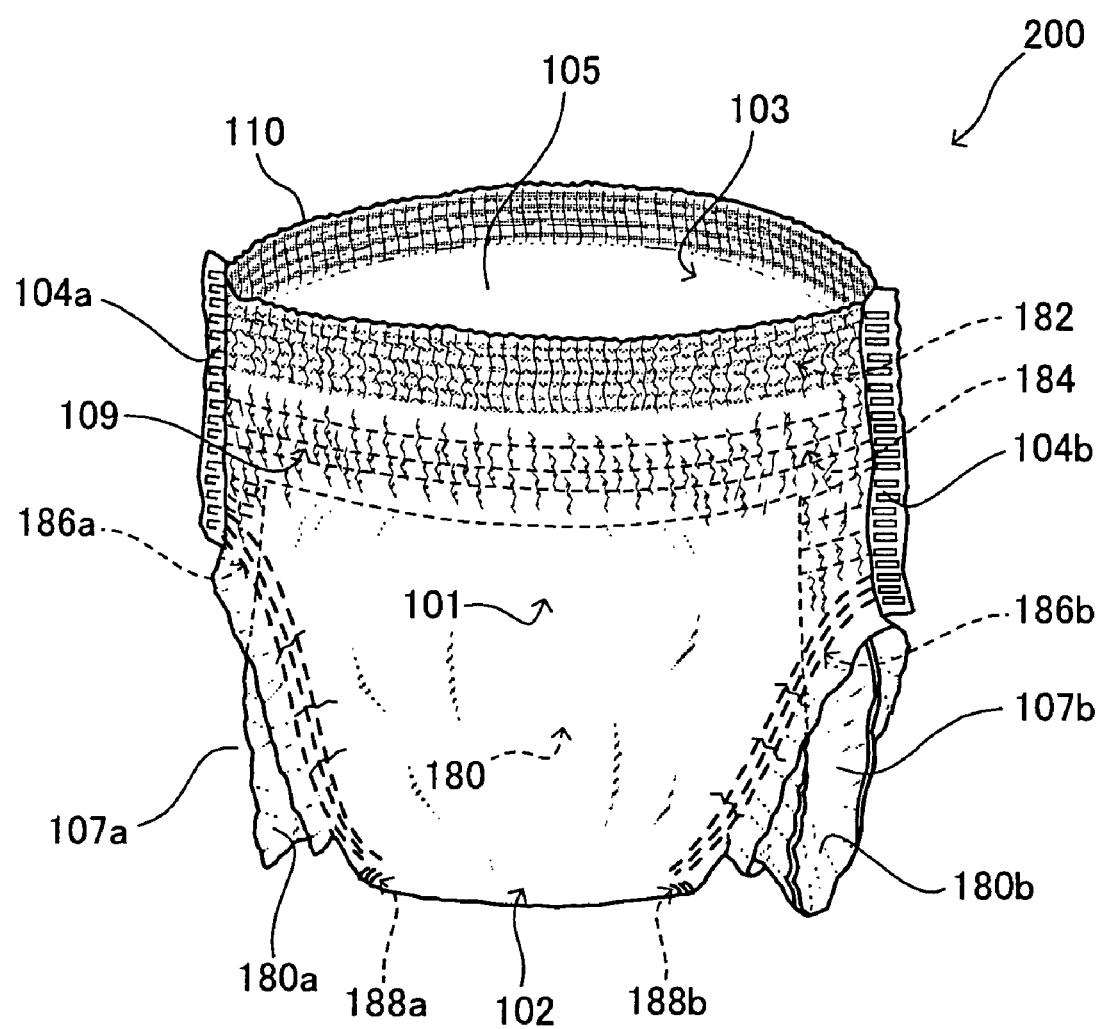
FIG. 4 is a perspective view schematically showing the state when a pull-on type disposable diaper in a second embodiment according to the present invention is worn.
Figure 5:
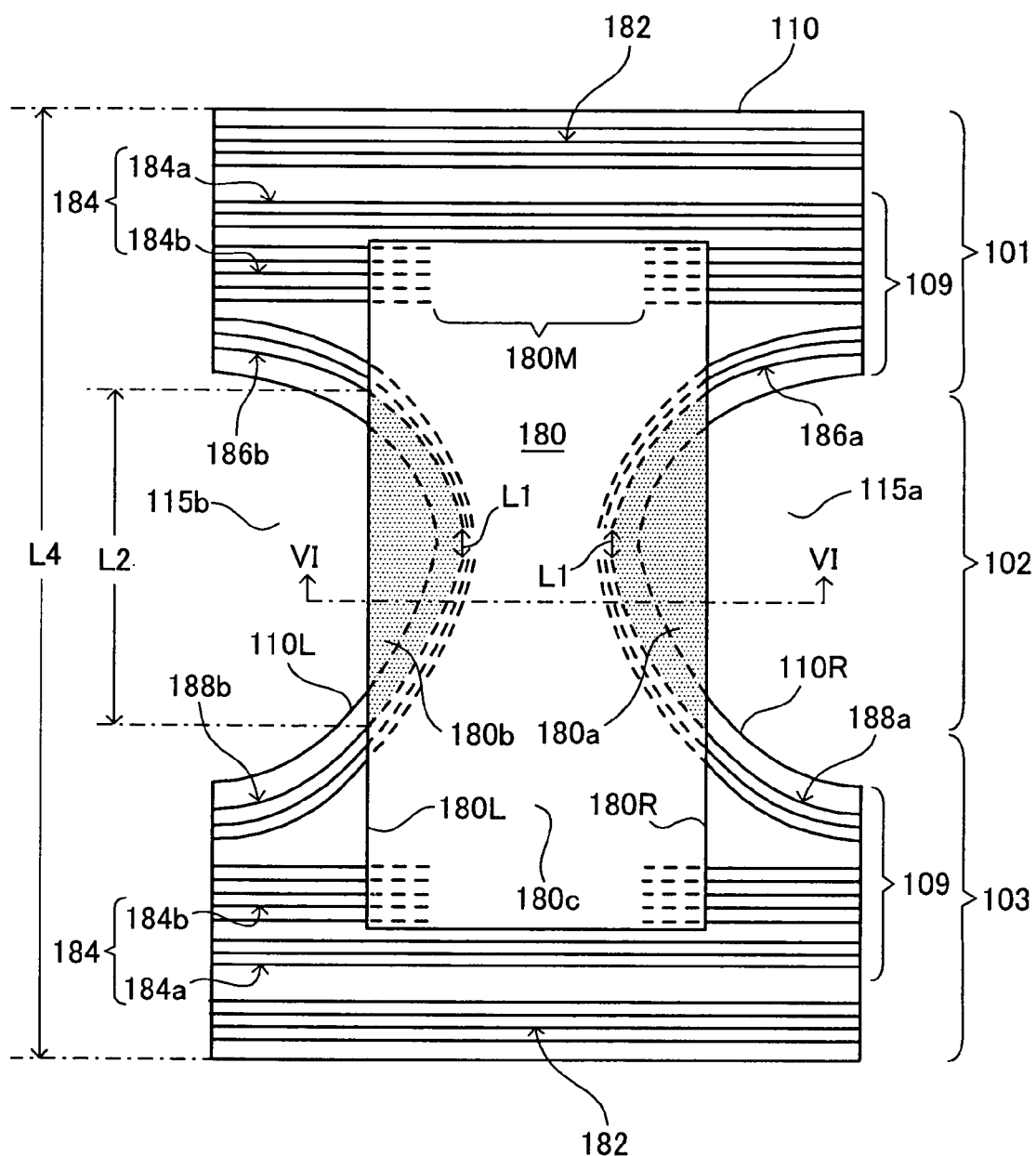
FIG. 5 is a plan view schematically showing the state when the pull-on type disposable diaper shown in FIG. 4 is expanded and held in a strained state, and is seen from the side which contacts with the skin of a wearer.
Figure 6:
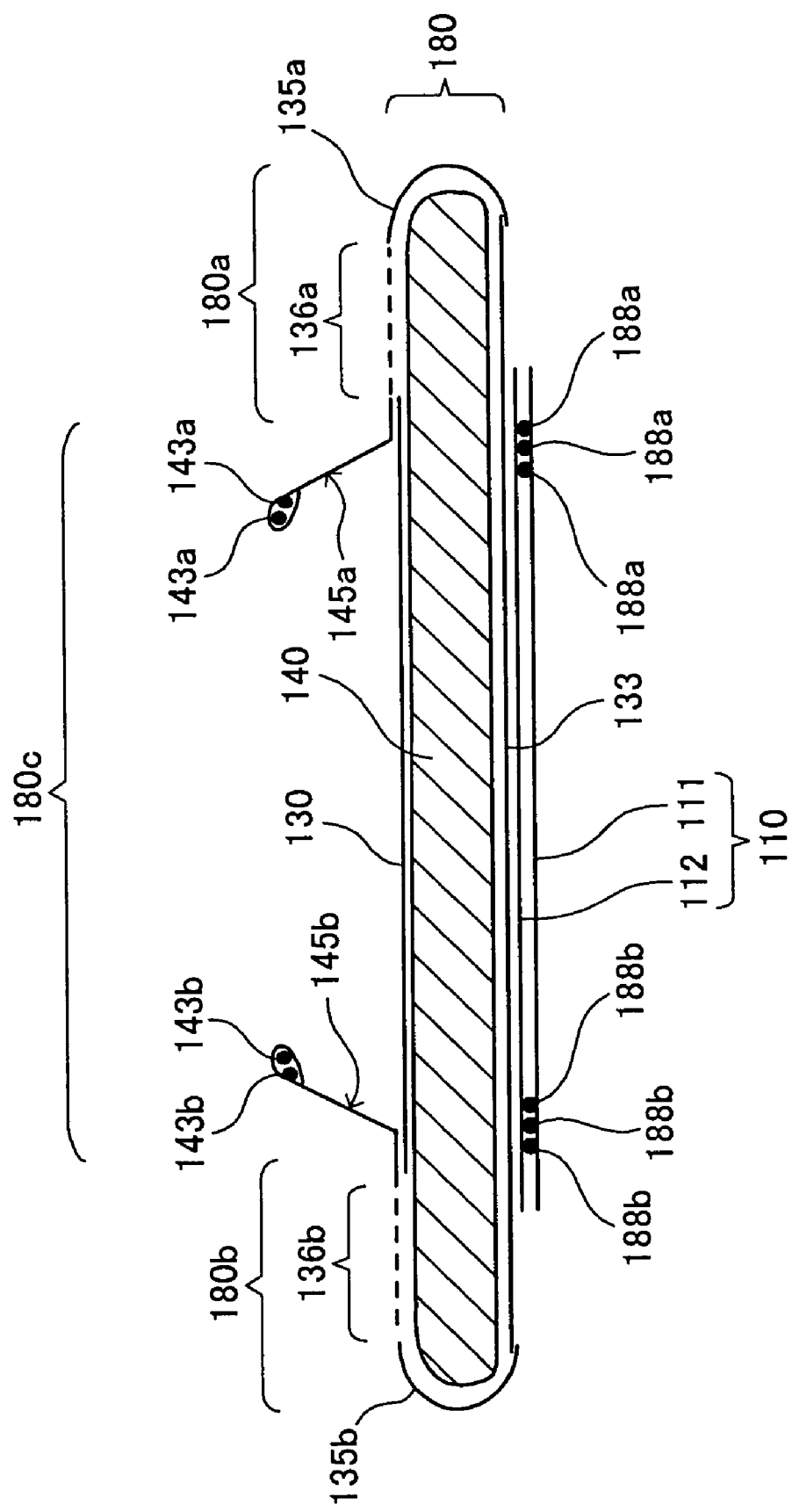
FIG. 6 is a schematic diagram of a section along the line VI—VI shown in FIG. 5.

FIG. 4 schematically shows the pull-on type disposable diaper 200 in a second embodiment in the worn state. FIG. 5 schematically shows the state when the pull-on type disposable diaper 200 shown in FIG. 4 is expanded and held in a strained state, and is seen from the side which contacts with the skin of a wearer. FIG. 6 schematically shows a section of the pull-on type disposable diaper 200 along the line VI—VI shown in FIG. 5.

In the pull-on type disposable diaper 200 in this embodiment, in order to increase the absorption ability of an absorbent article body 180, the width of the absorbent article body 180 is wider than that of the outer layer sheet 110 in a part of the crotch portion 102. The other configuration of the pull-on type disposable diaper 200 is the same as that of the pull-on type disposable diaper 100 in the first embodiment. Therefore, the constructional elements and areas shown in FIG. 4 to FIG. 6 having the same functions as those shown in FIG. 1 to FIG. 3 are denoted by the same reference symbols used with 100, and the description thereof is omitted. In FIG. 5, illustration of the first three-dimensional guards 145a and 145b is omitted, for convenience sake.

The minimum width of the absorbent article body 180 in the crotch portion 102 in the pull-on type disposable diaper 200 is selected within the range of from about 250 mm to 350 mm, as in the absorbent article body 80 in the pull-on type disposable diaper 100 in the first embodiment. And preferably, the minimum width thereof is selected within the range of from 270 mm to 310 mm.

Respective first leg portion elastic members 186a and 186b, and respective second leg portion elastic members 188a and 188b are isolated from each other in the crotch portion 102.

Therefore, the pull-on type disposable diaper 200 in this embodiment exhibits similar technical effects as those of the pull-on type disposable diaper 100 in the first embodiment.

Moreover, since the width of the absorbent article body 180 is wider than that of the outer layer sheet 110 in a part of the crotch portion 102, the comfort of the diaper and the fit of each respective leg flap absorbent articles 180a and 180b are improved as compared to the pull-on type disposable diaper 100 in the first embodiment. As a result, the performance of preventing leakage from the crotch portion 102 can be further improved.

The width of the absorbent article body 180 in the crotch portion 102 is preferably within the range of from 1.1 to 4.0 times, and more preferably, from 1.2 to 2.4 times as wide as the minimum width of the outer layer sheet 110 in the crotch portion 102, taking into consideration the comfort of the diaper and the fit of the respective leg flap absorbent articles 180a and 180b. The maximum exposed length (length in the width direction) of the absorbent article body 180 exposed from the outer layer sheet 110, as seen from the outer layer sheet 110 side, is preferably within the range of from 20 mm to 130 mm, and more preferably, within the range of from 30 mm to 95 mm, taking the comfort of the diaper into consideration.

The width of the respective leg flap absorbent articles 180a and 180b is preferably such that the lower limit is at least 10 mm, and more preferably, is at least 40 mm, and the upper limit is not more than 100 mm, in the portion where the width thereof is widest, taking into consideration the absorbing performance of the respective leg flap absorbent articles 180a and 180b.

The length L2 (see FIG. 5) in the longitudinal direction of the respective leg flap absorbent articles 180a and 180b is preferably within the range of from about ⅕ to ⅔, and more preferably, from ¼ to ½, with respect to the length L4 in the longitudinal direction of the diaper, as in the leg flap absorbent articles 80a and 80b in the pull-on type disposable diaper 100 of the first embodiment. Moreover, the gap L1 (see FIG. 4) between the first leg portion elastic members 186a, 186b and the second leg portion elastic members 188a, 188b is preferably selected within the same numerical range as that of the gap L1 (see FIG. 2) in the pull-on type disposable diaper 100 of the first embodiment.

THIRD EMBODIMENT

Figure 7:
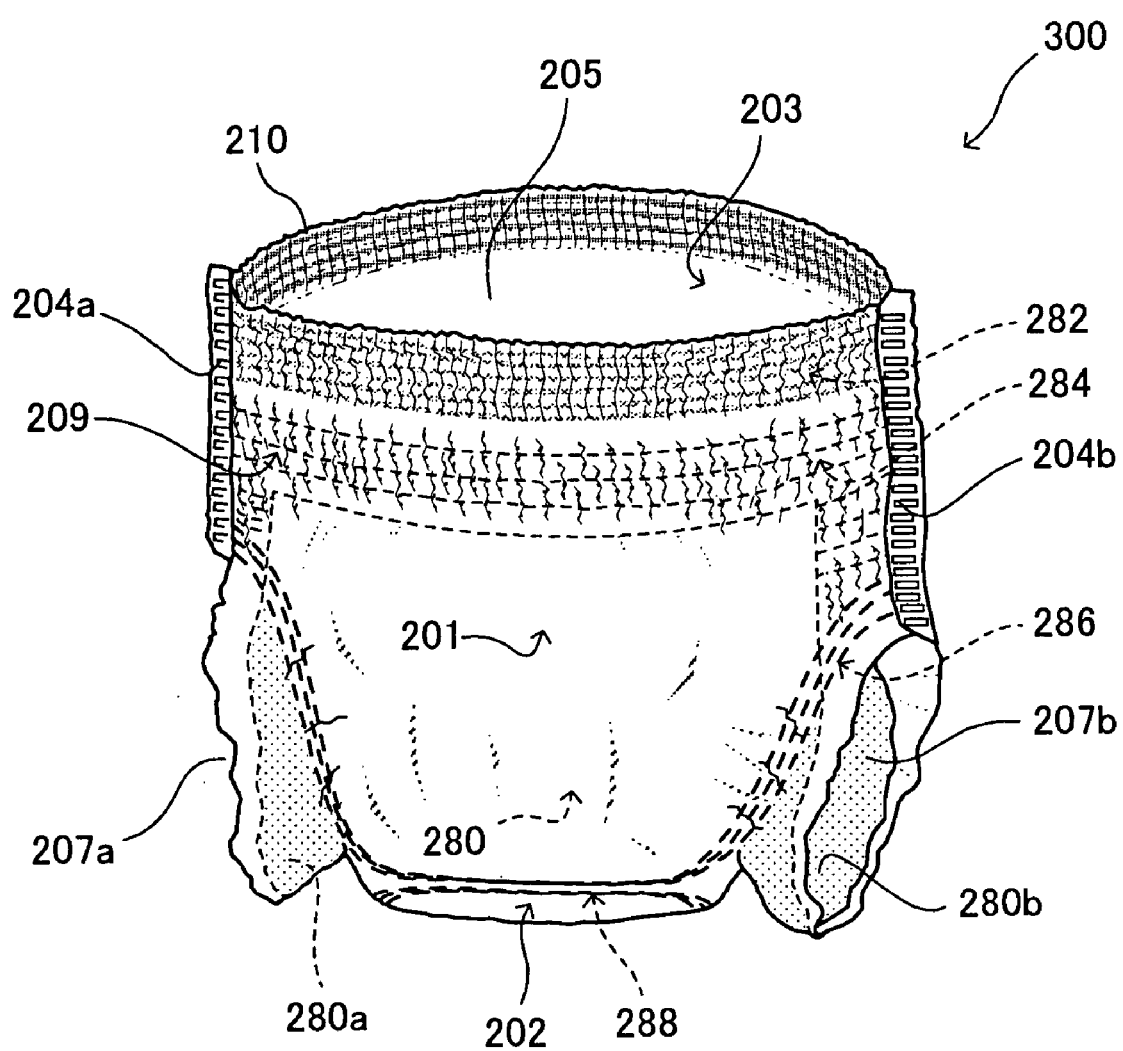
FIG. 7 is a perspective view schematically showing the state when a pull-on type disposable diaper in a third embodiment according to the present invention is worn.
Figure 8:
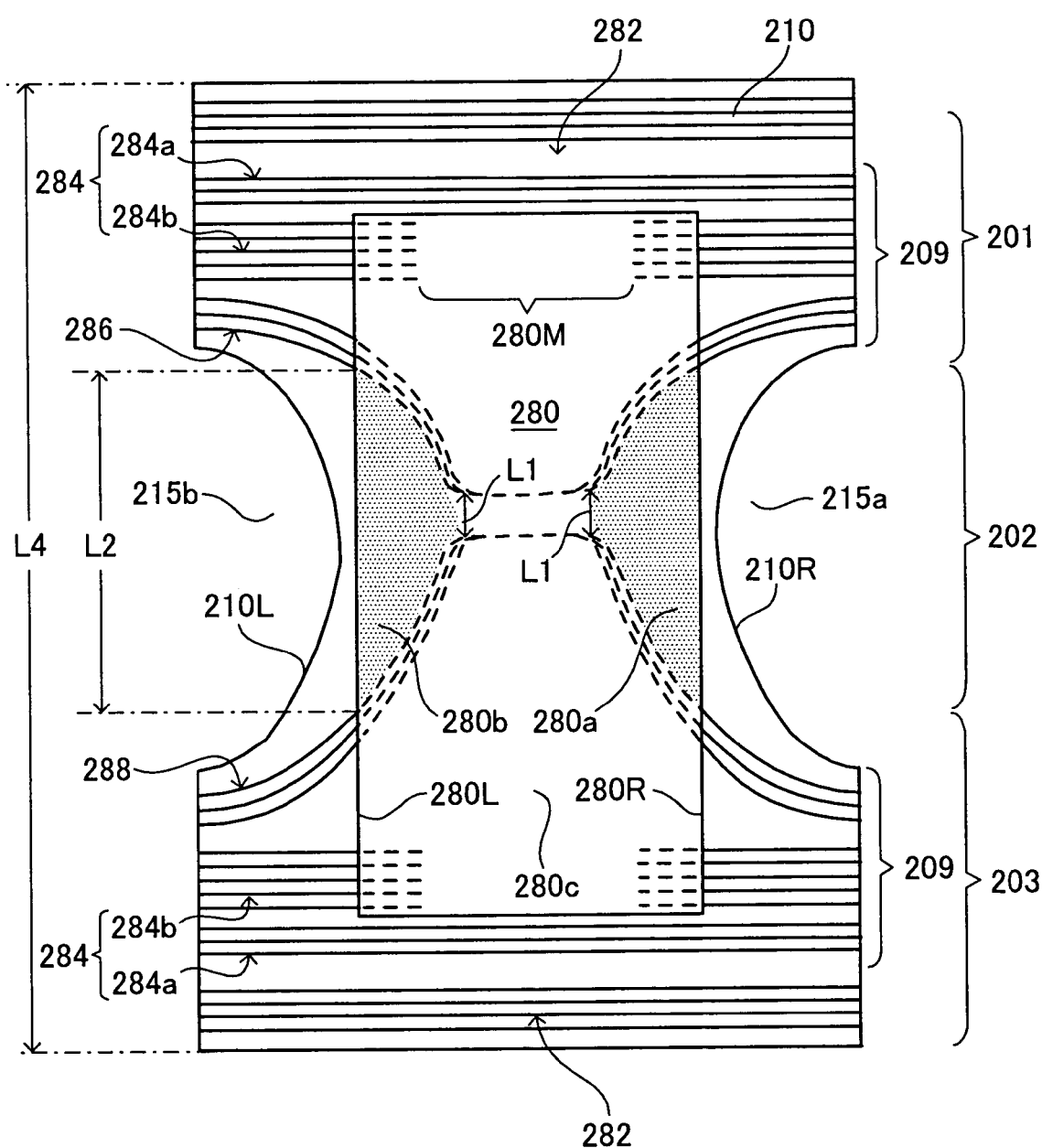
FIG. 8 is a plan view schematically showing the state when the pull-on type disposable diaper shown in FIG. 7 is expanded and held in a strained state, and is seen from the side which contacts with the skin of a wearer.

FIG. 7 schematically shows the state when a pull-on type disposable diaper 300 in the third embodiment is worn. FIG. 8 schematically shows the state when the pull-on type disposable diaper 300 shown in FIG. 7 is expanded and held in a strained state, and is seen from the side which contacts with the skin of a wearer.

The pull-on type disposable diaper 300 in this embodiment has the same configuration as that of the pull-on type disposable diaper 100 in the first embodiment, except for the shape of the respective leg portion elastic members. The constructional elements or areas shown in FIG. 7 and FIG. 8 having the same functions as those shown in FIG. 1 to FIG. 3 are denoted by the same reference symbols added with 200, and the description thereof is omitted.

The first leg portion elastic members are denoted by new reference symbol 286, and the second leg portion elastic members are denoted by new reference symbol 288. Though not shown, a pair of first three-dimensional guards is provided right and left in the width direction of the pull-on type disposable diaper 300, as in the pull-on type disposable diaper 100 in the first embodiment.

In the pull-on type disposable diaper 300, the first leg portion elastic members provided along a leg opening 207a and the first leg portion elastic members provided along a leg opening 207b are continuous in the crotch portion 202. Similarly, the second leg portion elastic members provided along the leg opening 207a and the second leg portion elastic members provided along the leg opening 207b are continuous in the crotch portion 202.

Specifically, the respective first leg portion elastic members 286 and the respective second leg portion elastic members 288 are formed by one elastic material, which extends from the leg opening 207a through the crotch portion 202 to the leg opening 207b. The respective leg portion elastic members 286 and 288 have an area extending substantially parallel with each other in the width direction of the pull-on type disposable diaper 300 in the crotch portion 202, and circular arc areas continue on the right and left opposite ends thereof.

The gap L1 (see FIG. 8) between the first leg portion elastic members 286 and the second leg portion elastic members 288 at the crotch portion 202 is selected within the same numerical range as that of the gap L1 in the pull-on type disposable diaper 100 of the first embodiment. The length L2 (see FIG. 8) in the longitudinal direction of the respective leg flap absorbent articles 280a and 280b is selected within the same numerical range as the length L2 in the pull-on type disposable diaper 100 of the first embodiment.

When the first leg portion elastic members or the second leg portion elastic members have an area extending linearly or curvilinearly in the width direction of the diaper, in the crotch portion, the "gap L1 between the first leg portion elastic members and the second leg portion elastic members in the crotch portion" refers to a gap between the edges of the respective leg portion elastic members in the crotch portion, of the area where a contraction stress works in a direction parallel with the longitudinal direction of the diaper.

The pull-on type disposable diaper 300 having the above-described configuration exhibits the same technical effects as those of the pull-on type disposable diaper 100 in the first embodiment.

Figure 9:
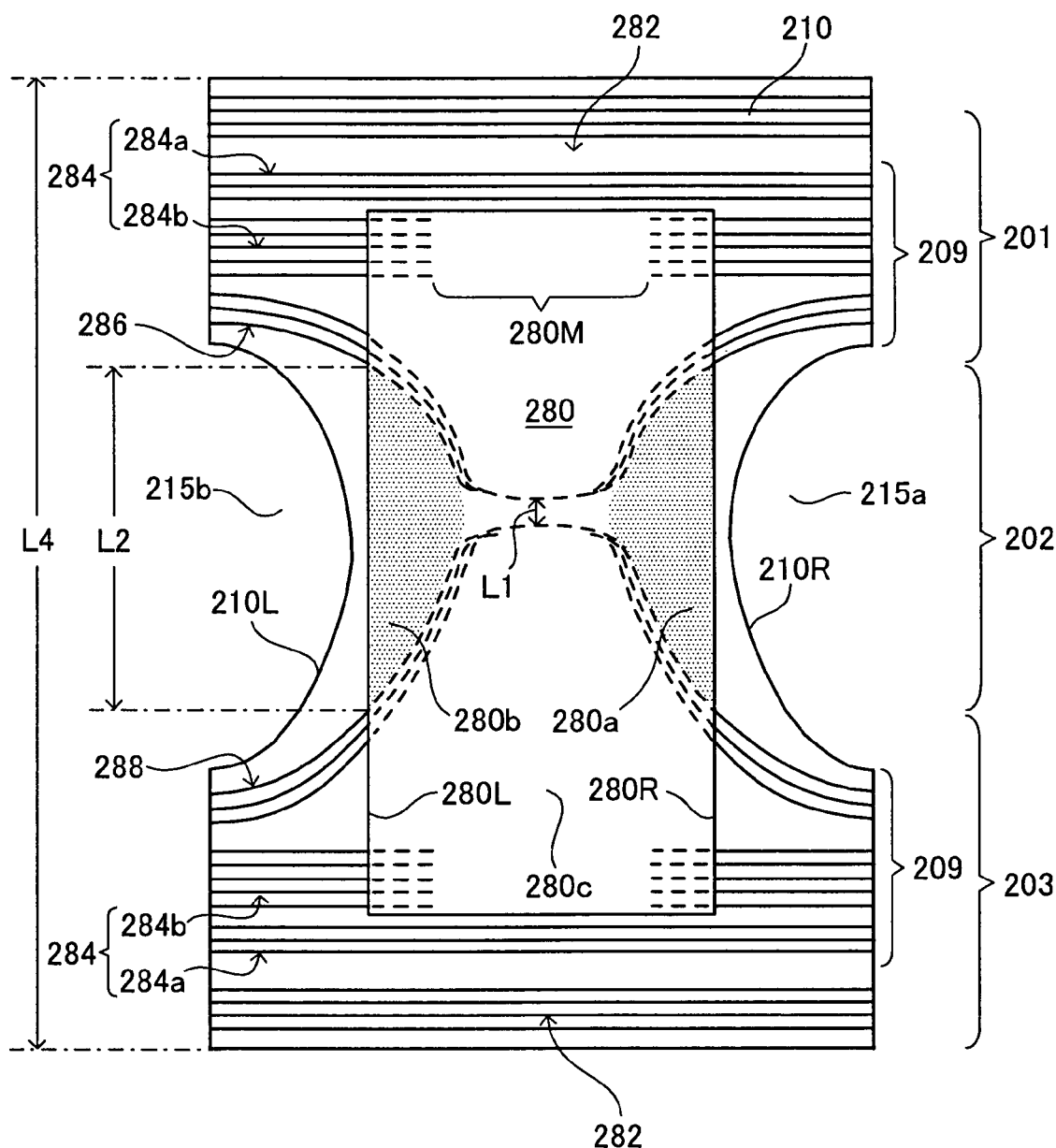
FIG. 9 is a plan view schematically showing the state when one modified example of the pull-on type disposable diaper shown in FIG. 7 is expanded and held in a strained state, and is seen from the side which contacts with the skin of a wearer.

Further, as shown in FIG. 9, similar technical effects can be obtained, even when the respective first leg portion elastic members 286 and the respective second leg portion elastic members 288 are arranged so as to draw a gradual curve in the crotch portion 202.

FOURTH EMBODIMENT

Figure 10:
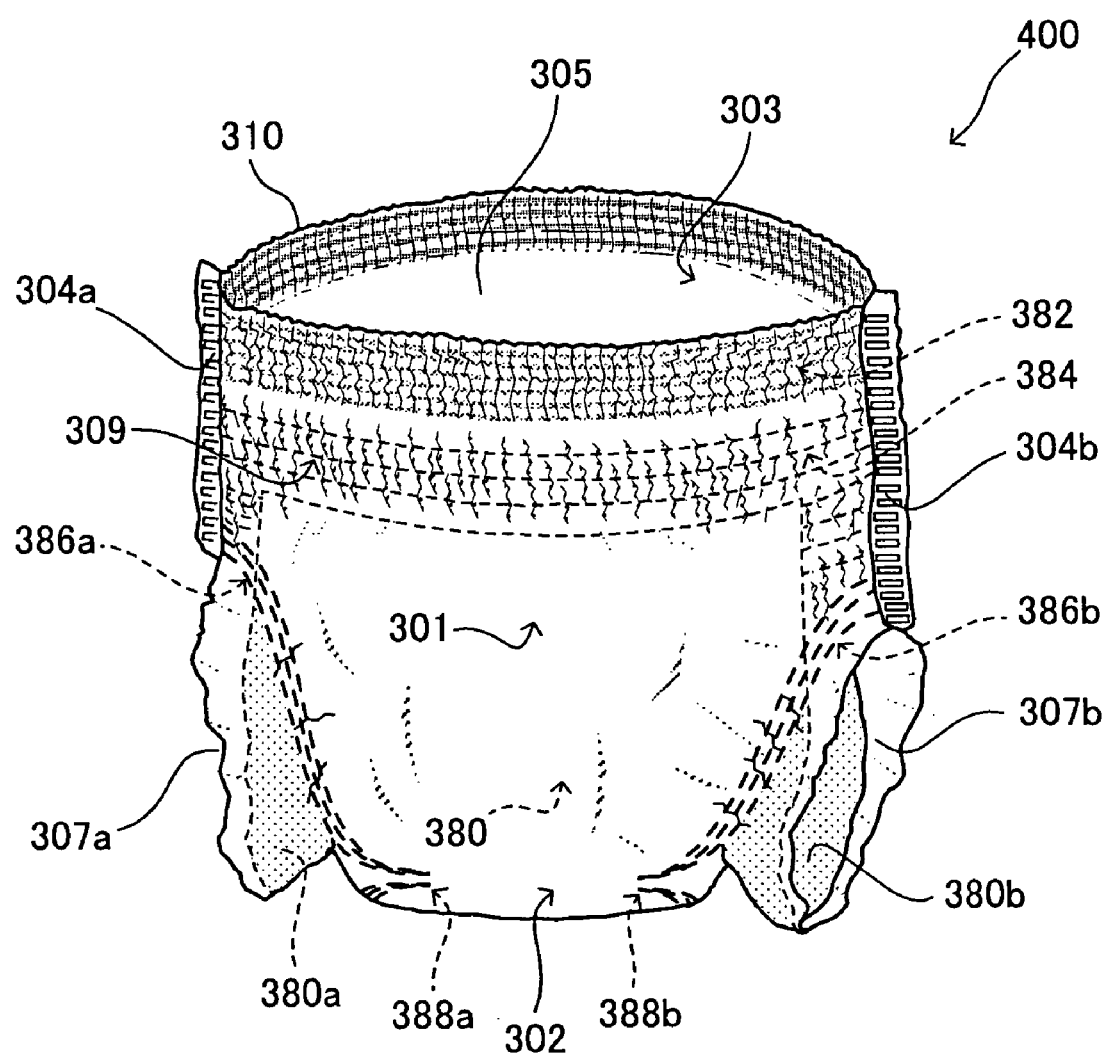
FIG. 10 is a perspective view schematically showing the state when a pull-on type disposable diaper in a fourth embodiment according to the present invention is worn.
Figure 11:
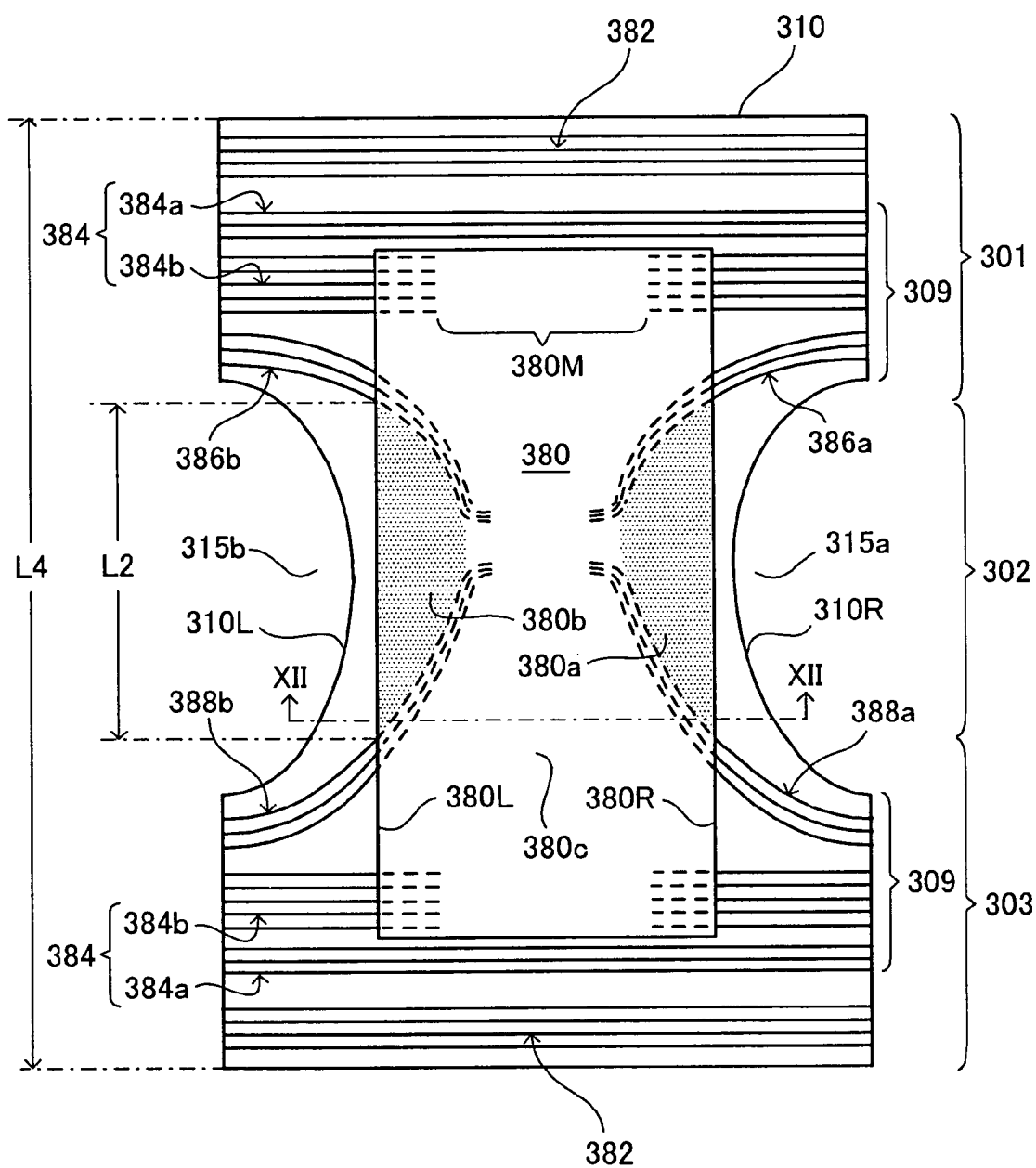
FIG. 11 is a plan view schematically showing the state when the pull-on type disposable diaper shown in FIG. 10 is expanded and held in a strained state, and is seen from the side which contacts with the skin of a wearer.
Figure 12:
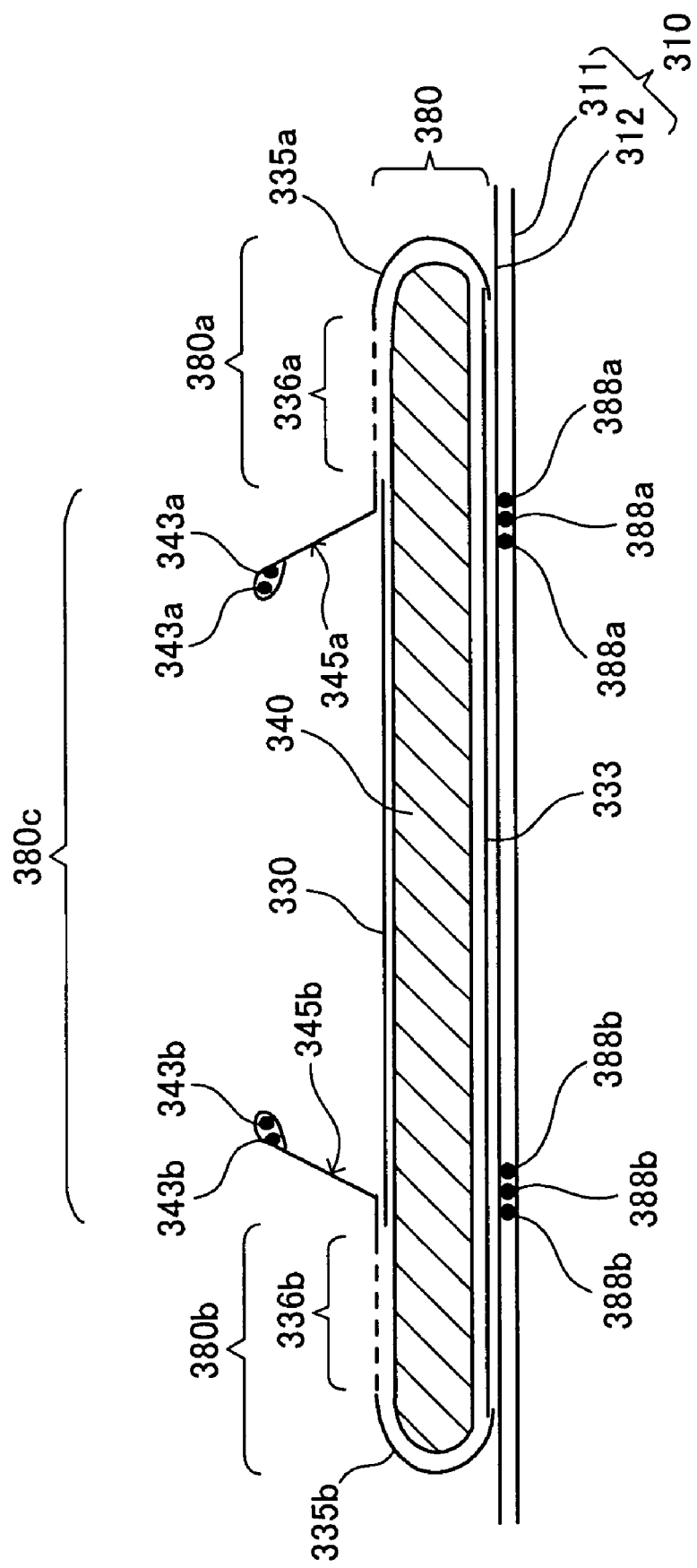
FIG. 12 is a schematic diagram of a section along the line XII—XII shown in FIG. 11.

FIG. 10 schematically shows a pull-on type disposable diaper 400 in the fourth embodiment, when worn. FIG. 11 schematically shows the state when the pull-on type disposable diaper 400 shown in FIG. 10 is expanded and held in a strained state, and is seen from the side which contacts with the skin of a wearer. FIG. 12 schematically shows a section of the pull-on type disposable diaper 400 along the line XII—XII shown in FIG. 11.

In the pull-on type disposable diaper 400 in this embodiment, areas extending in the width direction are formed at the respective ends of the first leg portion elastic members and the second leg portion elastic members in the crotch portion. The other configuration is the same as that of the pull-on type disposable diaper 100 in the first embodiment. The constructional elements and areas shown in FIG. 10 to FIG. 12 having the same functions as those shown in FIG. 1 to FIG. 3 are denoted by the same reference symbols added with 300, and the description thereof is omitted. The first leg portion elastic members are denoted by new reference symbols 386a and 386b, and the second leg portion elastic members are denoted by new reference symbols 388a and 388b. In FIG. 11, illustration of the first three-dimensional guards 345a and 345b is omitted, for convenience sake.

The pull-on type disposable diaper 400 having the above-described configuration exhibits the same technical effects as those of the pull-on type disposable diaper 100 in the first embodiment.

Further, in the pull-on type disposable diaper 400, (1) the respective first leg portion elastic members 386a and 386b, and the respective second leg portion elastic members 388a and 388b have the areas extending in the width direction; and (2) the respective second girth elastic members 384b (see FIG. 11) are arranged so as not to form any elastic flexibility in the central part 380M in the width direction of the absorbent article body 380 in the state shown in FIG. 11, as in the second girth elastic members 84b (see FIG. 2) in the pull-on type disposable diaper 100 in the first embodiment. Hence, gathers (not shown) are formed, though small, in the respective leg flap absorbent articles 380a and 380b. As a result, the respective leg flap absorbent articles 380a and 380b and the vicinity thereof can relatively expand and contract in the width direction at the time of wearing the pull-on type disposable diaper 400.

On the other hand, in the central portion in the width direction of the absorbent article body 380, since there is no elastic member extending in the width direction, the central portion cannot relatively expand and contract in the width direction.

As a result, in the central portion in the width direction of the absorbent article body 380, wrinkles are not likely to occur at the time of wearing the pull-on type disposable diaper 400, thereby improving the absorbing efficiency of the body waste. As a result, it is possible to further improve the performance of preventing leakage from the crotch portion 302.

In pull-on type disposable diapers for adults, which may be used together with an auxiliary pad, the following advantages can be obtained.

Figure 13:
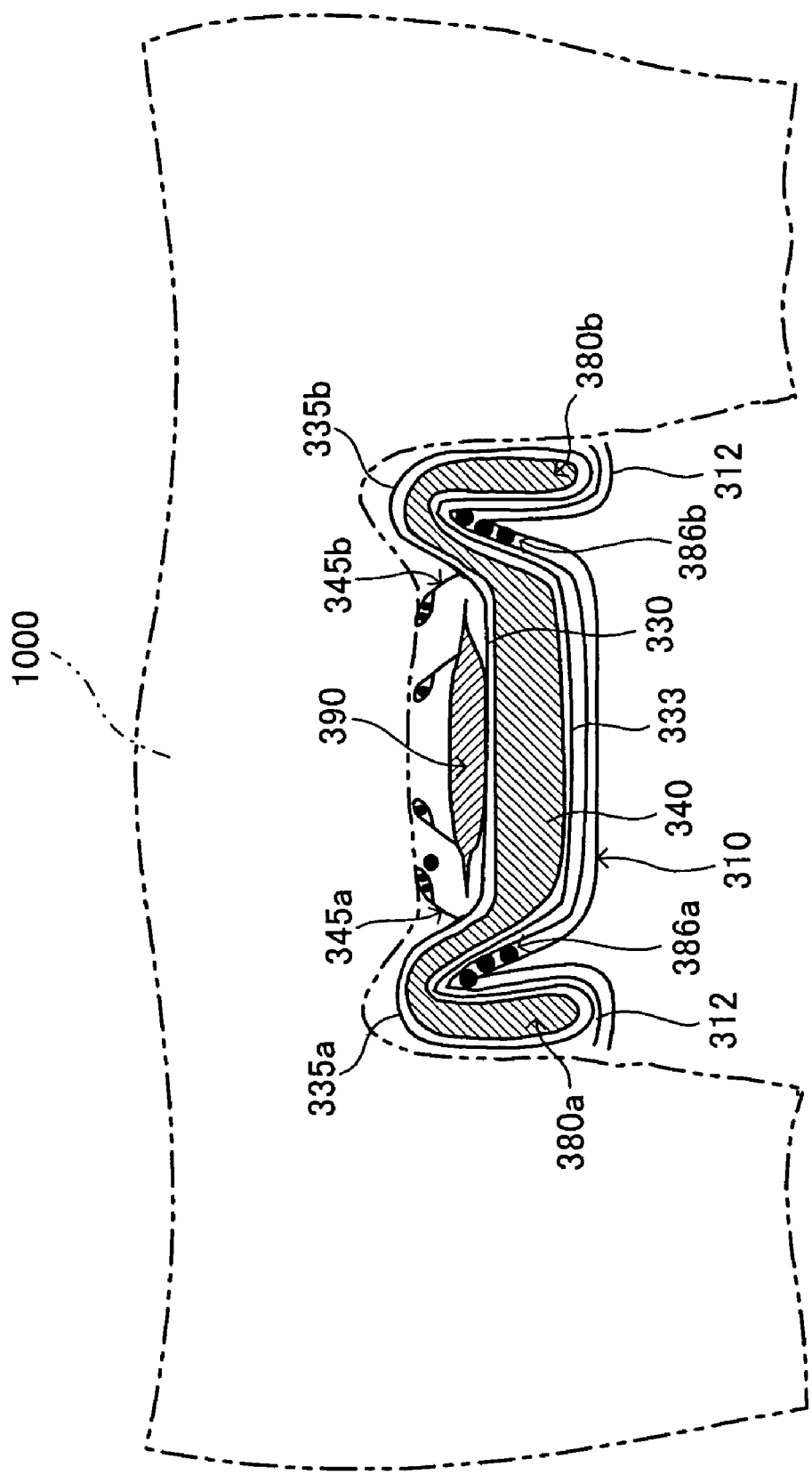
FIG. 13 is a cross section schematically showing the state of a crotch portion at the time of wearing the pull-on type disposable diaper shown in FIG. 10.

That is, as shown in FIG. 13, the auxiliary pad 390 is attached between the first three-dimensional guards 345a and 345b, and applied to the crotch of a wearer 1000. In the pull-on type disposable diaper 400, since the second girth elastic members 384b are arranged so as not to form any elastic flexibility of the respective second girth elastic members 384b in the central part 380M in the width direction of the absorbent article body 380, attachment of the auxiliary pad 390 becomes easy. This point also applies to the respective pull-on type disposable diapers 100, 200 and 300 in the first to the third embodiments.

In order to obtain the pull-on type disposable diaper 400 having a practical absorbing performance, it is preferred that the width of the area capable of relatively expanding or contracting in the absorbent article body 380 be within the range of from about ¼ to ⅔, and more preferably, about ⅓ of the width of the absorbent article body 380.

For that purpose, it is preferred that the width of the respective leg flap absorbent articles 380a and 380b be within the range of from about ⅙ to ⅓, and more preferably, about ¼ of the width of the absorbent article body 380.

FIRST MODIFIED EXAMPLE

Figure 14:
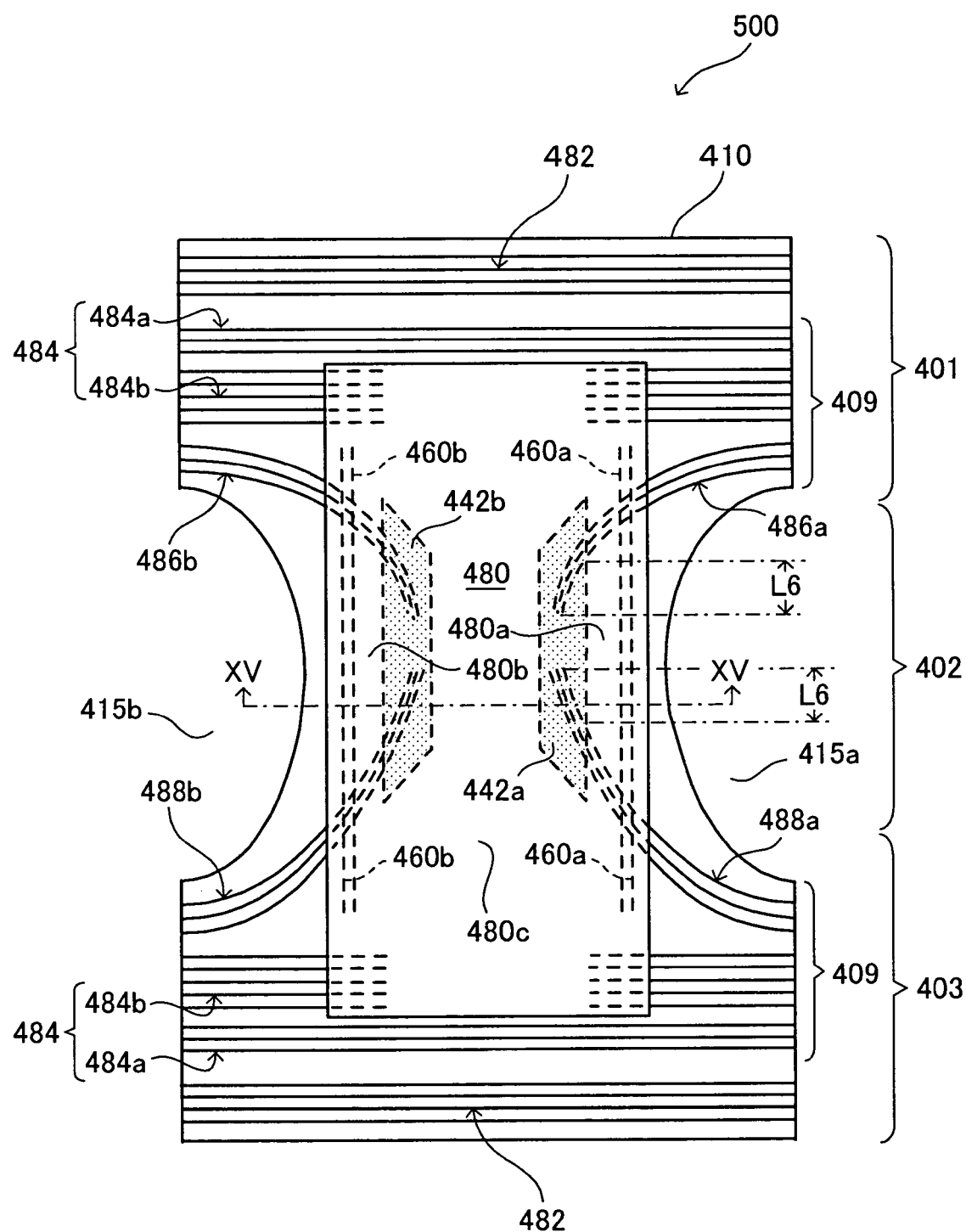
FIG. 14 is a plan view schematically showing the state when a pull-on type disposable diaper in a first modified example according to an embodiment of the present invention is expanded and held in a strained state, and is seen from the side which contacts with the skin of a wearer.
Figure 15:
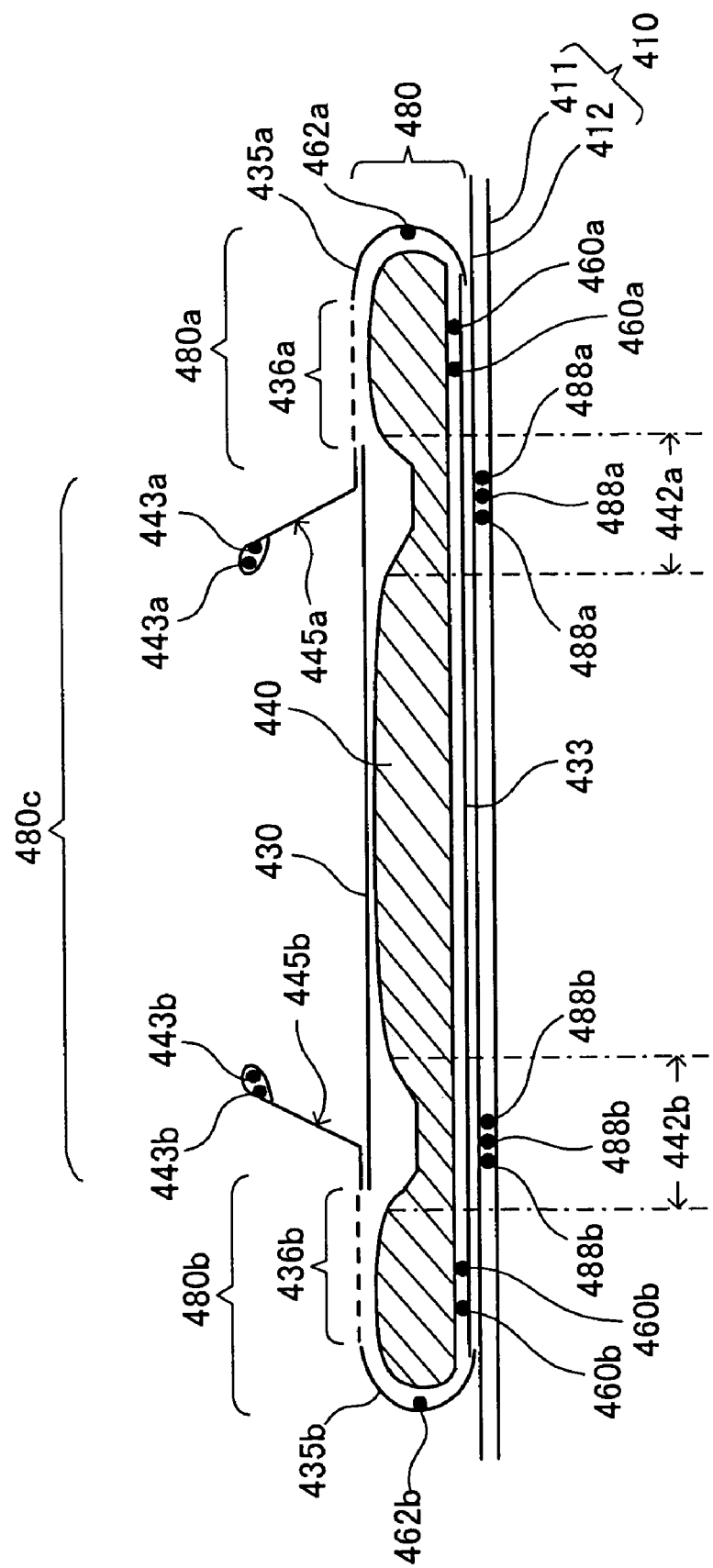
FIG. 15 is a schematic diagram of a section along the line XV—XV shown in FIG. 14.

FIG. 14 schematically shows the state when a pull-on type disposable diaper 500 according to the first modified example is expanded and held in a strained state, and is seen from the side which contacts with the skin of a wearer. FIG. 15 schematically shows a section of the pull-on type disposable diaper 500 along the line XV—XV shown in FIG. 14.

The pull-on type disposable diaper 500 in this modified example has an absorbent article body 480 having a structure different from that of the absorbent article body 80 in the pull-on type disposable diaper 100 in the first embodiment. The other structure is the same as that of the pull-on type disposable diaper 100 in the first embodiment, and the illustration when worn is omitted. The constructional elements or areas shown in FIG. 14 or FIG. 15 having the same function as those shown in FIG. 2 or FIG. 3 are denoted by the reference symbols added 400 to those of FIG. 2 or FIG. 3, and the description thereof is omitted. In FIG. 14, illustration of respective first three-dimensional guards 445a and 445b is omitted for the convenience sake. In FIG. 14, shading is not added to the respective leg flap absorbent articles 480a and 480b.

The absorbent article body 480 in the pull-on type disposable diaper 500 is different from the absorbent article body 80 in the pull-on type disposable diaper 100 in the first embodiment with regards to the following points. That is, (1) leg flap elastic members 460a and 460b are arranged so as to extend in the longitudinal direction of the leg flap absorbent articles 480a and 480b, on the external surface side (on the outer layer sheet 410 side) of the leg flap absorbent articles 480a and 480b; (2) leg flap side elastic members 462a and 462b are arranged so as to extend in the longitudinal direction of the leg flap absorbent articles 480a and 480b, at the outside edges in the width direction of the respective leg flap absorbent articles 480a and 480b; and (3) bending devices 442a and 442b which assist bending of the opposite side edges in the width direction of the absorbent article body 480, to form the side flap absorbent articles 480a and 480b, at the time of wearing the pull-on type disposable diaper 500 are provided. The elastic members and the bending devices will be described below in detail.

(1) Leg Flap Elastic Members and Leg Flap Side Elastic Members

The illustrated leg flap elastic members 460a and 460b are arranged between an absorbent article 440 and a back sheet 443 in an extended state, and the leg flap side elastic members 462a and 462b (see FIG. 15) are arranged on the external surface of the side edge sheets 435a and 435b in an extended state.

These leg flap elastic members 460a and 460b and leg flap side elastic members 462a and 462b extend over from the front side portion 401 to the back side portion 403, so as to cross the corresponding leg flap absorbent articles 480a and 480b in the longitudinal direction, to further prevent leakage from the crotch portion 402 by improving the fit of the leg flap absorbent articles 480a and 480b around the legs of the wearer of the diaper.

Only one of the leg flap elastic members and the leg flap side elastic members may be provided, but it is preferred to use them both together. In the illustrated absorbent article body 480, two leg flap elastic members 460a, 460b are respectively arranged for each leg flap absorbent article 480a and 480b. However, when the leg flap elastic members 460a and 460b are arranged, the number thereof can be a desired number of at least one for each leg flap absorbent article 480a or 480b. The same thing applies to the number of the leg flap side elastic members 462a and 462b.

However, when the leg flap elastic members 460a and 460b or the leg flap side elastic members 462a and 462b are arranged, if the extending stress of these elastic members is too large, the leg flap absorbent articles 480a and 480b irregularly bend at the time of wearing the pull-on type disposable diaper 500, whereby the fit of the leg flap absorbent articles 480a and 480b around the legs of the wearer may be hampered.

In order to reliably improve the fit of the leg flap absorbent articles 480a and 480b around the legs of the wearer, it is preferred that the total extending stress (hereinafter referred to as "total extending stress I") of all the leg flap elastic members 460a and 460b corresponding to one leg flap absorbent article 480a or 480b be less than the total of the extending stress of all the first leg portion elastic members 486a and 486b and the extending stress of all the second leg portion elastic members 488a and 488b corresponding to the leg flap absorbent article 480a or 480b (hereinafter referred to as "total extending stress III"). Similarly, it is preferred that the total extending stress (hereinafter referred to as "total extending stress II") of all the leg flap side elastic members 462a and 462b corresponding to one leg flap absorbent article 480a or 480b be less than the total extending stress III corresponding to the leg flap absorbent article 480a or 480b.

Specifically, the total extending stress I is preferably within the range of from 30% to 99%, and more preferably, from 50% to 90% of the corresponding total extending stress III. Moreover, the respective total extending stress II is preferably within the range of from 10% to 80%, more preferably, from 30% to 70% of the corresponding total extending stress III.

The respective extending stress of the leg flap elastic members 460a and 460b, the leg flap side elastic members 462a and 462b, the first leg portion elastic members 486a and 486b and the second leg portion elastic members 488a and 488b is measured by the following manner.

That is, with respect to the portion of the leg flap absorbent article in the crotch portion of the diaper, a test piece is cut so that the length in the longitudinal direction under the contracted state is 100 mm, the load at the time of extending by 25% is measured by a tension tester (manufactured by Orientec Co., distance between chucks: 80 mm, test speed: 300 mm/min), which is converted to the width of the test piece, to obtain the respective extending stress.

For the leg flap elastic members 460a and 460b and the leg flap side elastic members 462a and 462b, filamentous elastic members (filar rubber or the like), belt-shaped elastic members (flat rubber or the like) having a predetermined width, or thin-film elastic members (urethane film or the like) may be used.

(2) Bending Devices

The bending devices 442a and 442b assists in bending the opposite side edges in the width direction of the absorbent article body 480 to form the side flap absorbent articles 480a and 480b, at the time of wearing the pull-on type disposable diaper 500. The bending devices 442a and 442b can be made by providing embossing finish in predetermined portions of the absorbent article body 480, or forming low-rigidity areas having relatively low rigidity in predetermined portions of the absorbent article body 480.

The above-described embossing finish is obtained by machining the surface of the absorbent article body so as to have texture, and by applying such embossing, the shape of the surface of the absorbent article body changes to become easy to bend. The area to be embossed is not particularly limited, so long as the embossed area is isolated from the side edges of the absorbent article body 480 toward the inner side in the width direction, at least in the crotch portion 402, but it is preferred to apply embossing, with a predetermined gap from the side edges of the absorbent article body 480, so that the width of the leg flap absorbent articles 480a and 480b have the above-described width.

The embossing may be applied by using, for example, an embossing roll. For the embossing roll to be used, a pair of rolls consisting of an engraving roll and a smoothing roll is generally used. For the engraving roll, for example, an iron roll, on the surface of which various patterns are engraved, can be used. On the other hand, for the smoothing roll, for example, a paper roll, a cotton roll, a rubber roll, an iron roll can be used.

When embossing is applied to the absorbent article body, the absorbent article body can be preheated by a heating roll beforehand. Moreover, the embossing roll itself may be heated, and the absorbent article body may be interposed between the heated rolls, to apply embossing. At the time of heating, it is preferred to set the temperature of the embossing roll to a temperature lower by at least 10° C. than the melting point of the material for forming the absorbent article body. Moreover, the linear load at the time of embossing is preferably within the range of from about 5×9.8 to 50×9.8 N/cm (5 to 50 kgf/cm), and more preferably from about 7×9.8 to 30×9.8 N/cm (7 to 30 kgf/cm), as a general range, though it depends on the thickness of the absorbent article body to be embossed, the heating temperature and the running speed.

On the other hand, when the bending devices 442a and 442b are provided in the absorbent article body by forming the low-rigidity areas in the absorbent article body, the forming method of the low-rigidity area is not particularly limited, so long as the rigidity in a part of the absorbent article body can be made lower than that of any other regions. For example, the low-rigidity area can be formed by the following methods, that is, (i) tearing out a part of the absorbent article body; (ii) making a part of the absorbent article 440 have a lower basis weight than that of the other regions; (iii) making a part of the absorbent article 440 thinner than other regions; (iv) forming a part of the absorbent article 440 by a more flexible material than that of the other regions. Moreover, by combining at least two of the methods (i) to (iv), the low-rigidity area can be formed. Among these methods, it is preferred to form the low-rigidity area by method (i) or (ii) above.

When the low-rigidity area is formed by the above method (i) or (ii), the ratio between the basis weight of the low-rigidity area and the basis weight of the absorbent article 440 in a region adjacent to the low-rigidity area on the inner side in the width direction, and the ratio between the basis weight of the low-rigidity area and the basis weight of the absorbent article 440 in a region adjacent to the low-rigidity area on the outer side in the width direction are preferably in the range of from 0 to 0.5. Moreover, a difference in the basis weight of the low-rigidity area and the absorbent article 440 in the area adjacent to the low-rigidity area on the inner side or the outer side in the width direction is preferably at least 100 g/m², and more preferably, at least 200 g/m².

The low-rigidity area is preferably formed such that when the pull-on type disposable diaper 500 is held in a strained state as shown in FIG. 14, and when the leg portion elastic member located outermost in the width direction, of the respective first leg portion elastic members 486a and 486b and second leg portion elastic members 488a and 488b corresponding to one leg opening 407a or 407b, is seen in plan view, the total of the length L6 of the portion within the bending device (low-rigidity area) 442a or 442b is preferably within the range of from 10 to 50%, and more preferably, from 20 to 40% of the length in the longitudinal direction of the absorbent article body 380. Further, it is preferred to form the low-rigidity area such that the total of the length L6 is within the range of from 5 to 40%, more preferably, from 15 to 30% of the length L4 in the longitudinal direction of the diaper. In FIG. 14, shading is added to the low-rigidity areas 442a and 442b, for easy understanding of the range of the low-rigidity areas 442a and 442b.

The pull-on type disposable diaper 500 in this modified example having the above-described structure exhibits the same technical effects as those of the pull-on type disposable diaper 100 in the first embodiment. Moreover, since the pull-on type disposable diaper 500 has leg flap elastic members 460a and 460b, leg flap side elastic members 462a and 462b, and bending devices 442a and 442b, the comfort and the prevention of leakage from the crotch portion 402 can be further improved, as compared with the pull-on type disposable diaper 100 in the first embodiment.

The bending devices 442a and 442b can be formed in the absorbent article body, whether or not the leg flap elastic members 460a and 460b, or the leg flap side elastic members 462a and 462b are provided.

The leg flap elastic members 460a and 460b, the leg flap side elastic members 462a and 462b, and the bending devices 442a and 442b can be provided in the absorbent article body, as in the absorbent article body 480 in this modified example, even when the first leg portion elastic members provided along one of the leg openings and the first leg portion elastic members provided along the other of the leg openings are made continuous in the crotch portion, and the second leg portion elastic members provided along one of the leg openings and the second leg portion elastic members provided along the other of the leg openings are also made continuous in the crotch portion, as in the pull-on type disposable diaper 300 in the third embodiment. In this case, the total extending stress III can be measured by the same method as the extending stress measuring method described above.

Figure 16:
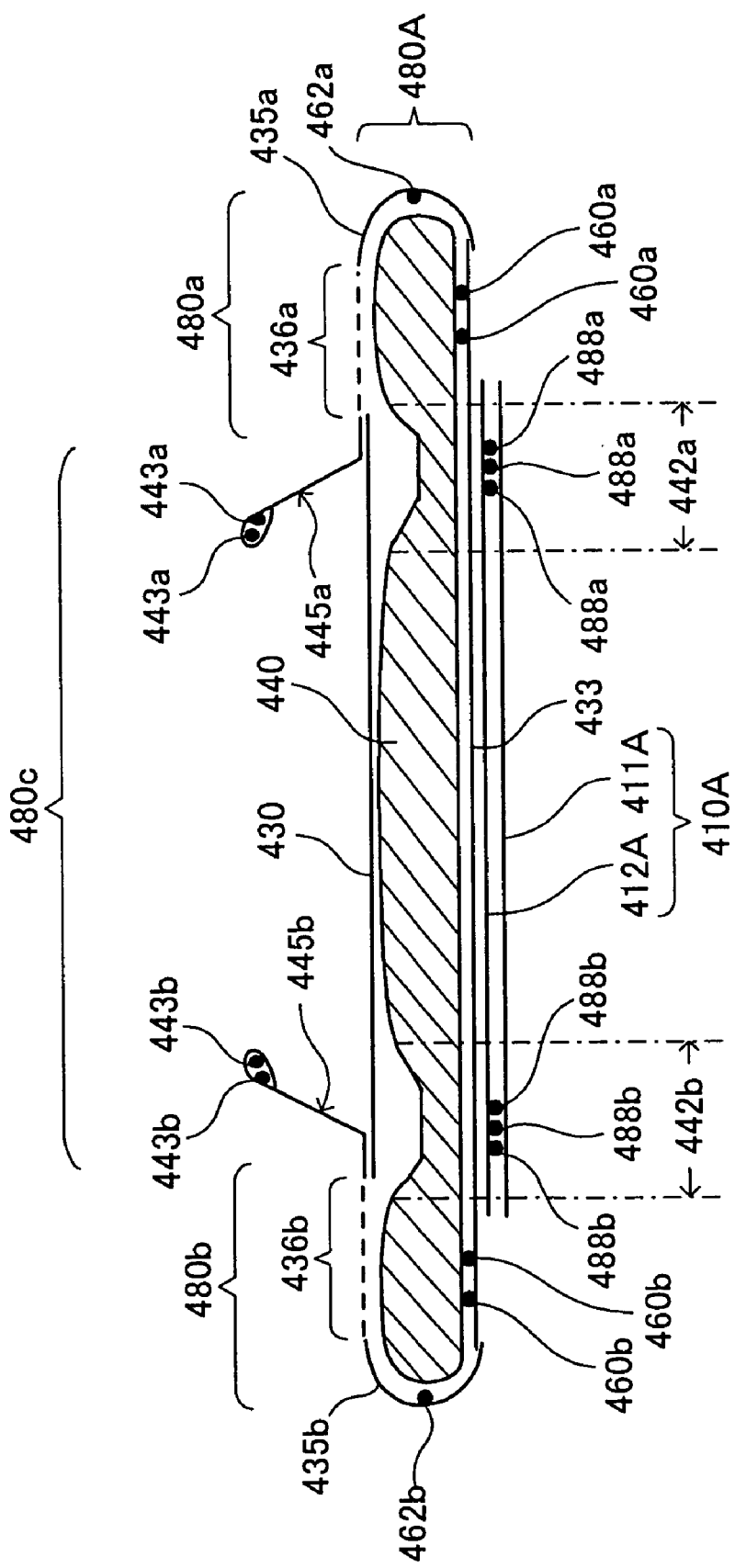
FIG. 16 is a schematic diagram of a section relating to one modified example according to the pull-on type disposable diaper shown in FIG. 14.

Further, as in an absorbent article body 480A shown in FIG. 16, in a part of the crotch portion, when the width of the absorbent article body 480A is made wider than the width of the outer layer sheet 410, as in the absorbent article body 180 of the pull-on type disposable diaper 200 in the second embodiment, the leg flap elastic members 460a and 460b, the leg flap side elastic members 462a and 462b, and the bending devices 442a and 442b can be used. The constructional elements shown in FIG. 16 having the same function as those shown in FIG. 6 are denoted by the reference symbols added 300 to those of FIG. 2 or FIG. 3, and the description thereof is omitted.

SECOND MODIFIED EXAMPLE

Figure 17:
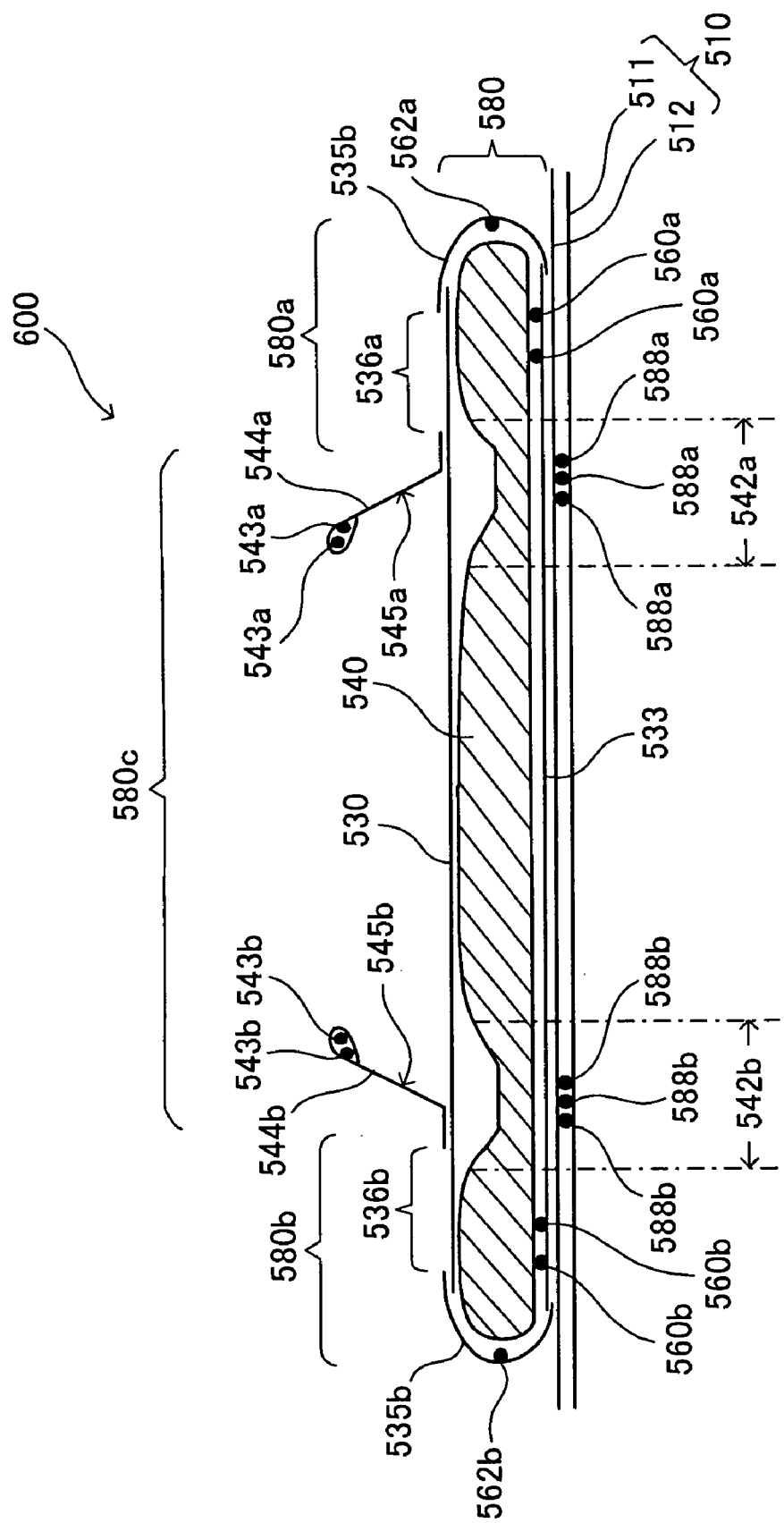
FIG. 17 is a schematic diagram of a section when a pull-on type disposable diaper in a second modified example according to an embodiment of the present invention is expanded and held in a strained state, and the disposable diaper is cut at a portion corresponding to the line III—III shown in FIG. 2.

FIG. 17 schematically shows a section where a pull-on type disposable diaper 600 in the second modified example is expanded and held in a strained state, and the disposable diaper is cut at a portion corresponding to the line III—III shown in FIG. 2.

In the pull-on type disposable diaper 600 in this modified example, the method of forming the side absorbing areas 536a and 536b and the first three-dimensional guards 545a and 545b is different from that of the side absorbing areas 36a and 36b, and the first three-dimensional guards 45a and 45b in the pull-on type disposable diaper 100 in the first embodiment. The other structure is the same as that of the pull-on type disposable diaper 100 in the first embodiment, and hence illustrations in the states of wearing it and of expanding and holding it in a strained state are omitted. Moreover, the constructional elements or areas shown in FIG. 17 having the same functions as those shown in FIG. 2 or FIG. 3 are denoted the reference symbols added 500 to those of FIG. 2 or FIG. 3, and the description thereof is omitted.

As shown in FIG. 17, the side absorbing areas 536a and 536b in the pull-on type disposable diaper 600 are formed by extending the top sheet 530 onto the side flap absorbent articles 580a and 580b. Liquid impermeable side edge sheets 535a and 535b are arranged on the outside in the width direction of the respective side absorbing areas 536a and 536b. Hereinafter, the area covered with the side edge sheets 535a and 535b on the outside in the width direction of the respective side absorbing areas 536a and 536b are referred to as "side areas". By providing the side areas, the body waste can be prevented from exuding from the side edges of the absorbent article body 580.

The respective first three-dimensional guards 545a and 545b have a structure such that one end in the width direction of the liquid impermeable sheet 544a, 544b is respectively fixed on the top sheet 530, and a desired number of elastic members 543a and 543b are arranged at the edge of the free end thereof in an extended state. In FIG. 17, respectively two elastic members 543a and 543b are shown.

For the sheets 544a and 544b, for example, those exemplified as the materials for the side edge sheets 35a and 35b in the description of the pull-on type disposable diaper 100 in the first embodiment can be used.

The pull-on type disposable diaper 600 in this modified example having such structure exhibits the same technical effects as those of the pull-on type disposable diaper 100 in the first embodiment.

The absorbent article body 580 having the structure shown in FIG. 17 is applicable for any of the pull-on type disposable diapers 100, 200, 300 and 400 of the first to fourth embodiments.

THIRD MODIFIED EXAMPLE

Figure 18:
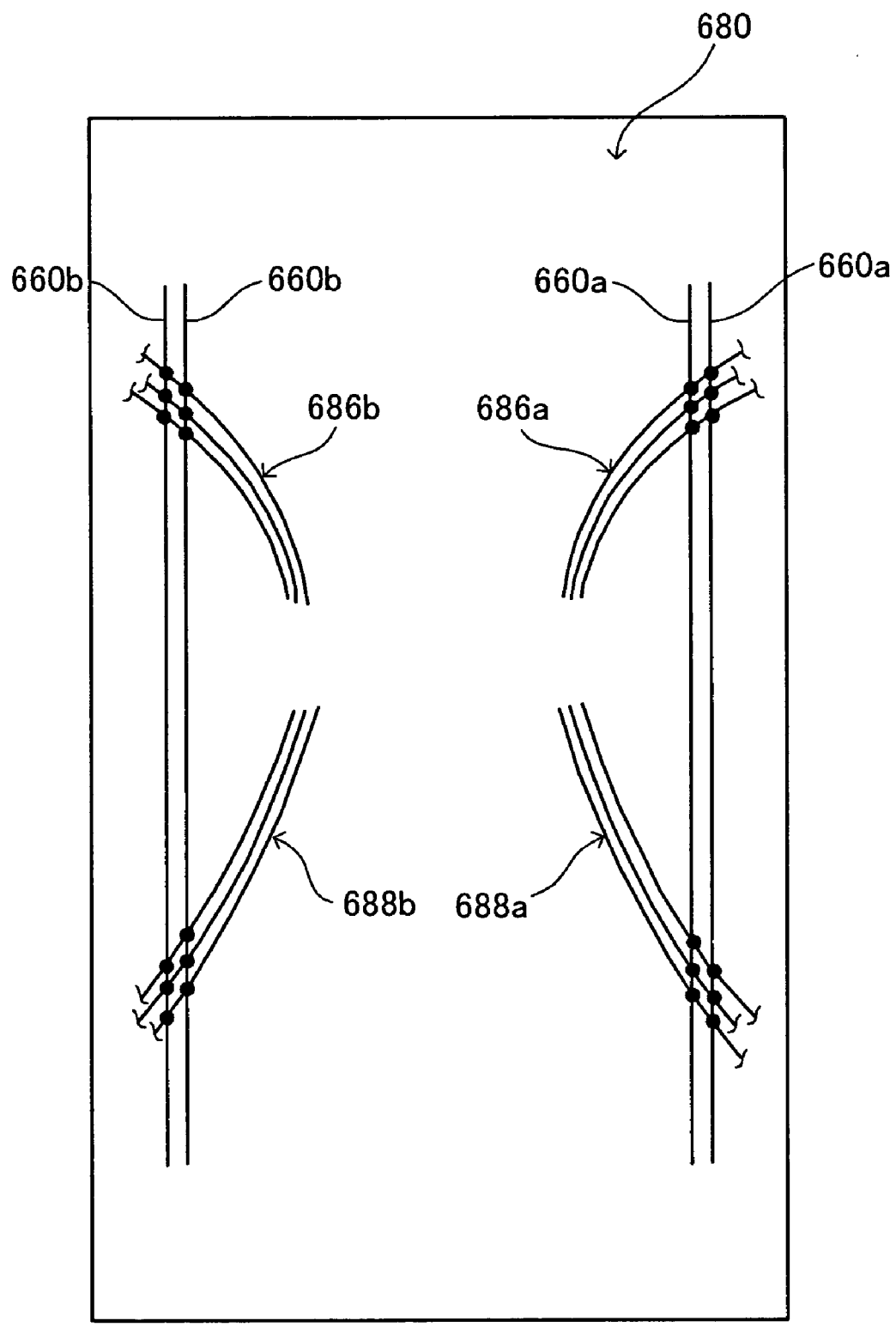
FIG. 18 is a plan view schematically showing one example of the relative relation between respective leg flap elastic members and respective first leg portion elastic members and respective second leg portion elastic members, when an absorbent article body in a pull-on type disposable diaper in a third modified example according to an embodiment of the present invention is held in a strained state.

FIG. 18 schematically shows the relative relation between the respective leg flap elastic members 660a and 660b, and the respective first leg portion elastic members 686a and 686b, and the respective second leg portion elastic members 688a and 688b, when the absorbent article body 680 in a pull-on type disposable diaper in the third modified example is held in a strained state.

The structure of the pull-on type disposable diaper in this modified example is the same as that of the pull-on type disposable diaper 100 in the first embodiment, except that the respective leg flap elastic members 660a contract, linked with the contraction of the respective first leg portion elastic members 686a and the respective second leg portion elastic members 688a, and the respective leg flap elastic members 660b contract, linked with the contraction of the respective first leg portion elastic members 686b and the respective second leg portion elastic members 688b. Therefore, illustrations of the state at the time of wearing the pull-on type disposable diaper in this modified example, and the state at the time of expanding and holding the diaper in a strained state are omitted.

The respective leg flap elastic members 660a are connected to the respective first leg portion elastic members 686a and the respective second leg portion elastic members 688a, and the respective leg flap elastic members 660b are connected to the respective first leg portion elastic members 686b and the respective second leg portion elastic members 688b, so that the leg flap elastic members 660a and 660b contract, linked with the contraction of the leg portion elastic members 686a, 686b, 688a and 688b. In FIG. 18, the connected portions of the leg flap elastic members and the leg portion elastic members are indicated by black dots.

The leg flap elastic members 660a, the first leg portion elastic members 686a and the second leg portion elastic members 688a may be directly connected to each other, or may be connected via the side edge sheet or the back sheet. Similarly, the leg flap elastic members 660b, the first leg portion elastic members 686b and the second leg portion elastic members 688b may be directly connected to each other, or may be connected via the side edge sheet, the back sheet or by an adhesive. The positions to provide the leg flap elastic members 660a and 660b are appropriately selected according to the connection form with the leg portion elastic members 686a, 686b, 688a and 688b.

The pull-on type disposable diaper in this modified example having such a structure exhibits the same technical effects as those of the pull-on type disposable diaper 100 in the first embodiment. Moreover, since the leg flap elastic members 660a and 660b contract, linked with the contraction of the leg portion elastic members 686a, 686b, 688a and 688b, the respective leg flap absorbent articles adhere to the inner parts of the thighs of the wearer, so as to follow the movement of the wearer. As a result, there is the effect that even when the wearer is active, the respective leg flap absorbent articles can be made to adhere to the inner parts of the thighs of the wearer effectively and naturally. Moreover, there is the technical effect that the shape holding property of the diaper when worn is improved, to prevent the diaper from getting out of shape.

In any of the pull-on type disposable diapers 100, 200, 300 and 400 in the first to fourth embodiments, the construction may be such that, linked with the contraction of the respective first leg portion elastic members and the respective second leg portion elastic members corresponding to one of the leg openings, the respective leg flap elastic members corresponding to the leg opening contract, and linked with contraction of the respective first leg portion elastic members and the respective second leg portion elastic members corresponding to the other leg opening, the respective leg flap elastic members corresponding to the other leg opening contract.

It is preferred to reduce the time difference from when the first leg portion elastic members 686a and 686b or the second leg portion elastic members 688a and 688b contract until the leg flap elastic members 660a and 660b contract, so that the respective leg flap absorbent articles are not largely apart from the inner parts of the thighs of the wearer, when worn. Moreover, it is preferred to construct the diaper such that the leg flap elastic members 660a and 660b contract largely in different directions, linked with the contraction of the respective first leg portion elastic members 686a and 686b, or the respective second leg portion elastic members 688a and 688b.

In order to reduce the time difference described above, the leg flap elastic members 660a, the first leg portion elastic members 686a and the second leg portion elastic members 688a, and the leg flap elastic members 660b, the first leg portion elastic members 686b and the second leg portion elastic members 688b are preferably connected with each other as shown in FIG. 18. It is also preferred to connect these in the manner of (1) or (2) described below. The explanation of (1) and (2) will be given for an example of the leg flap elastic members 660a and the first leg portion elastic members 686a corresponding thereto.

Figure 19:
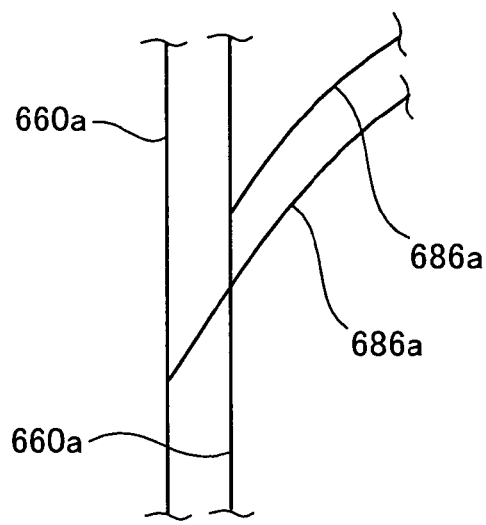
FIGS. 19A and 19B are plan views schematically showing other examples of the relative relation between the respective leg flap elastic members and the respective first leg portion elastic members and the respective second leg portion elastic members, when an absorbent article body in a pull-on type disposable diaper in the third modified example according to an embodiment of the present invention is held in a strained state.
Figure 19:
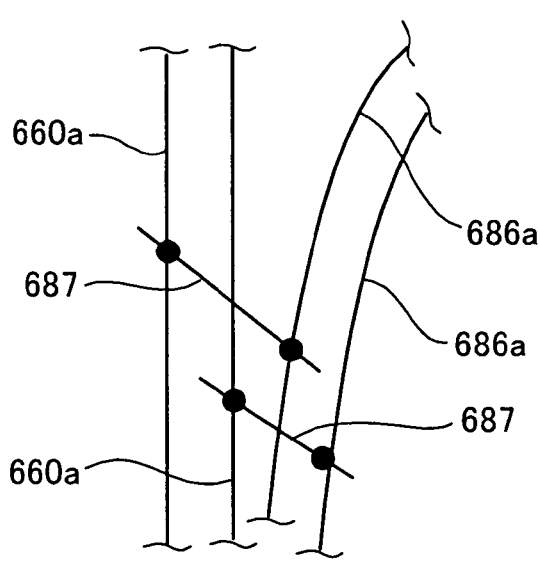

(1) As shown in FIG. 19A, the leg flap elastic members 660a and the first leg portion elastic members 686a are integrally formed of one elastic material.

(2) As shown in FIG. 19B, the leg flap elastic members 660a and the first leg portion elastic members 686a are connected with each other via inelastic members 687. Black dots in FIG. 19B indicates the connection points of the two members.

Furthermore, in order to allow the leg flap elastic members 660a and 660b to contract largely and in different directions as much as possible, linked with the contraction of the first leg portion elastic members 686a and 686b or the second leg portion elastic members 688a and 688b, if the inelastic members 687 shown in FIG. 19B are not used, it is preferred to set the angle between the leg portion elastic members 686a, 688a and the leg flap elastic members 660a, and the angle between the leg portion elastic members 686b, 688b and the leg flap elastic members 660b within the range of about 15 to 75 degrees, respectively. When the inelastic members 687 shown in FIG. 19B are used, the angle between the inelastic members 687 and the leg flap elastic members 660a and 660b is preferably within the range of about 15 to 75 degrees.

The above "angle" refers to an angle, which is smaller of the two kinds of angles formed by making the two members cross each other or connecting the two members, as seen in plan view. When at least one of the two members is curved, it is assumed that the angle is defined by using the intersection of these members as seen in plan view or the tangent of the curved member at the connection point.

If the above angle is roughly less than 15°, the leg portion elastic members 686a, 686b, 688a and 688b and the leg flap elastic members 660a and 660b contract substantially in the same direction, and hence the adhesion of the leg flap absorbent articles to the inner parts of the thighs of the wearer is likely to decrease. If the above angle roughly exceeds 75°, the linkage between the leg portion elastic members 686a, 688a and the leg flap elastic members 660a, and the linkage between the leg portion elastic members 686b, 688b and the leg flap elastic members 660b decrease, thereby the adhesion of the leg flap absorbent articles to the inner parts of the thighs of the wearer is likely to decrease. Therefore, it is further desirable to set the angle within the range of from about 15 to about 45°.

FOURTH MODIFIED EXAMPLE

Figure 20:
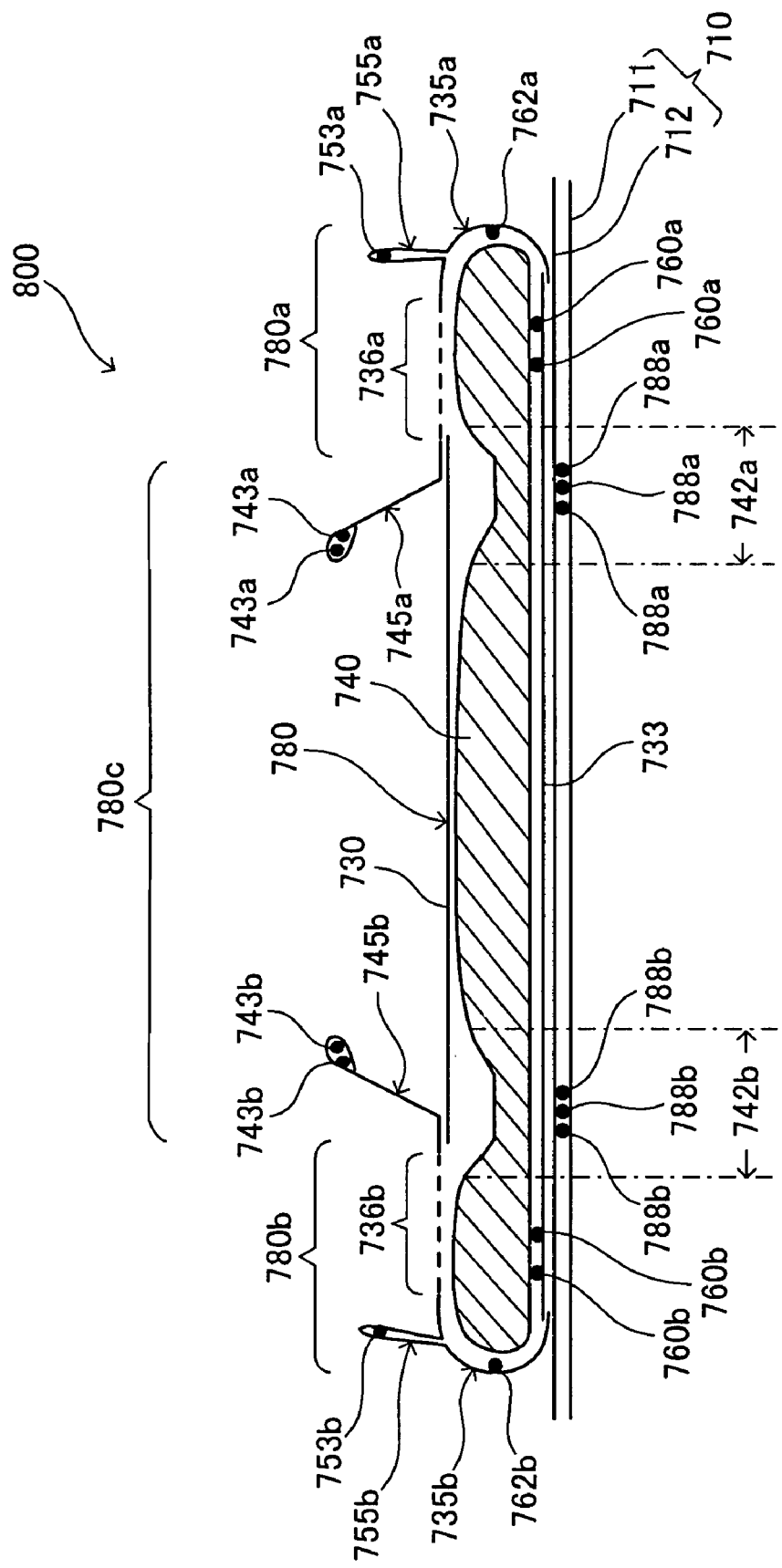
FIG. 20 is a schematic diagram of a section when a pull-on type disposable diaper in a fourth modified example according to an embodiment of the present invention is expanded and held in a strained state, and the disposable diaper is cut at a portion corresponding to the line III—III shown in FIG. 2.

FIG. 20 schematically shows a section when a pull-on type disposable diaper 800 according to the fourth modified example is expanded and held in a strained state, and the disposable diaper is cut at a portion corresponding to the line III—III shown in FIG. 2.

In the pull-on type disposable diaper 800 in this modified example, as shown in the figure, second three-dimensional guards 755a and 755b are formed outside the side absorbing areas 736a and 736b. The other configuration is the same as that of the pull-on type disposable diaper 500 in the first modified example. The constructional elements shown in FIG. 20 having the same function as those shown in FIG. 15 are denoted by the reference symbols added 300 to those of FIG. 15, and the description thereof is omitted.

The respective second three-dimensional guards 755a and 755b are formed by putting the elastic members 753a and 753b between the side edge sheets 735a, and at least at the time of wearing the pull-on type disposable diaper 800, the second three-dimensional guards 755a and 755b stand up on the leg flap absorbent articles 780a and 780b outside the corresponding side absorbing areas 736*a* and 736*b*. In FIG. 20, the first three-dimensional guards 745*a* and 745*b* and the second three-dimensional guards 755*a* and 755*b* are shown in the standing state, but when the pull-on type disposable diaper 800 is expanded and held in a strained state, the respective first three-dimensional guards 745*a* and 745*b* lay flat on the top sheet 730, and the respective second three-dimensional guards 755*a* and 755*b* lay flat on the corresponding leg flap absorbent articles 780*a* and 780*b*.

The pull-on type disposable diaper 800 having such configuration exhibits the same technical effects as those of the pull-on type disposable diaper 500 in the first modified example. Moreover, since the pull-on type disposable diaper 800 has the second three-dimensional guards 755*a* and 755*b*, prevention of leakage from the crotch portion becomes easier.

In order to maximize the leak prevention effect by the second three-dimensional guards 755*a* and 755*b*, it is preferred to set the height when the second three-dimensional guards 755*a* and 755*b* are in a standing up position within the range of from about 3 to about 20 mm, and more preferably, from about 3 to about 10 mm. If the height of the second three-dimensional guards 755*a* and 755*b* while in a standing up position exceeds 20 mm, there are problems in that the adhesion of the leg flap absorbent articles 780*a* and 780*b* to the inner parts of the thighs of the wearer decreases, and the second three-dimensional guards 755*a* and 755*b* may be turned up at the time of wearing the diaper.

On the other hand, the height of the first three-dimensional guards 745*a* and 745*b* while in a standing up position is preferably within the range of from about 20 to about 60 mm, and more preferably, from about 25 to about 45 mm. By setting the height within the above range, it becomes easy to make the first three-dimensional guards 745*a* and 745*b* reliably adhere to the skin of the wearer. This similarly applies to the case where only the first three-dimensional guards are provided, without forming the second three-dimensional guards. Similarly, in any case whether the first three-dimensional guards and the second three-dimensional guards are both formed, or when only the first three-dimensional guards are formed, the opposite ends in the longitudinal direction of the respective three-dimensional guards are preferably fixed to the top sheet or the side edge sheet, over the whole length of the three-dimensional guards, in order to obtain a desired leak prevention effect. Moreover, it is preferred that the length of the first three-dimensional guards and the second three-dimensional guards be longer than that in the longitudinal direction of the respective leg flap absorbent articles, from a standpoint of improving the leak prevention effect.

Figure 21:
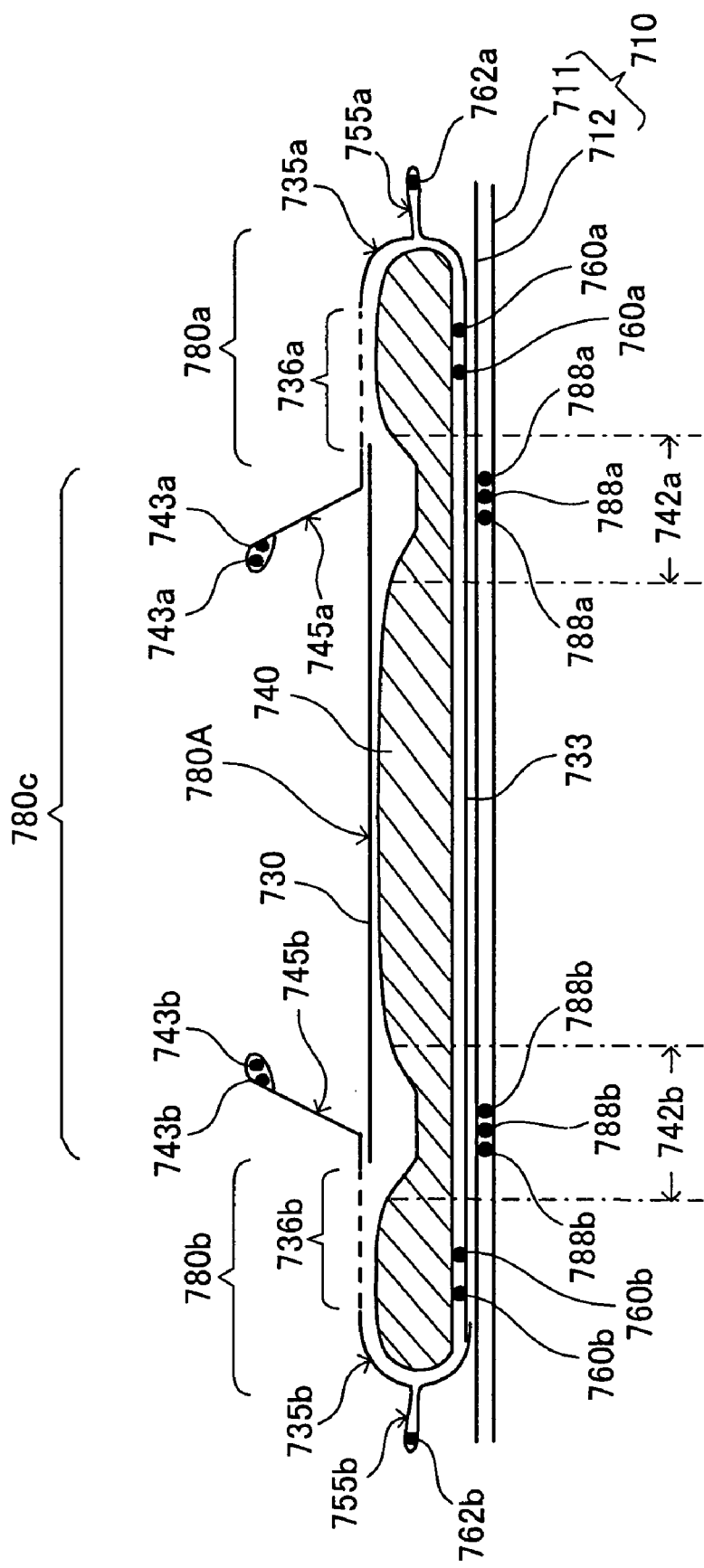
FIG. 21 is a schematic diagram of a section relating to one modified example of the pull-on type disposable diaper shown in FIG. 20.

As in an absorbent article body 780A shown in FIG. 21, second three-dimensional guards 755*a* and 755*b* may be formed so as to protrude outside in the width direction on the side of the leg flap absorbent articles 780*a* and 780*b*. In this case, the leg flap side elastic members 762*a* and 762*b* can be used as the elastic members for the second three-dimensional guards 757*a* and 757*b*.

The second three-dimensional guards may be formed by using the side edge sheets, or may be formed on the side edge sheet by using a special sheet, as in the first three-dimensional guards 545*a* and 545*b* shown in FIG. 17.

FIFTH MODIFIED EXAMPLE

Figure 22:
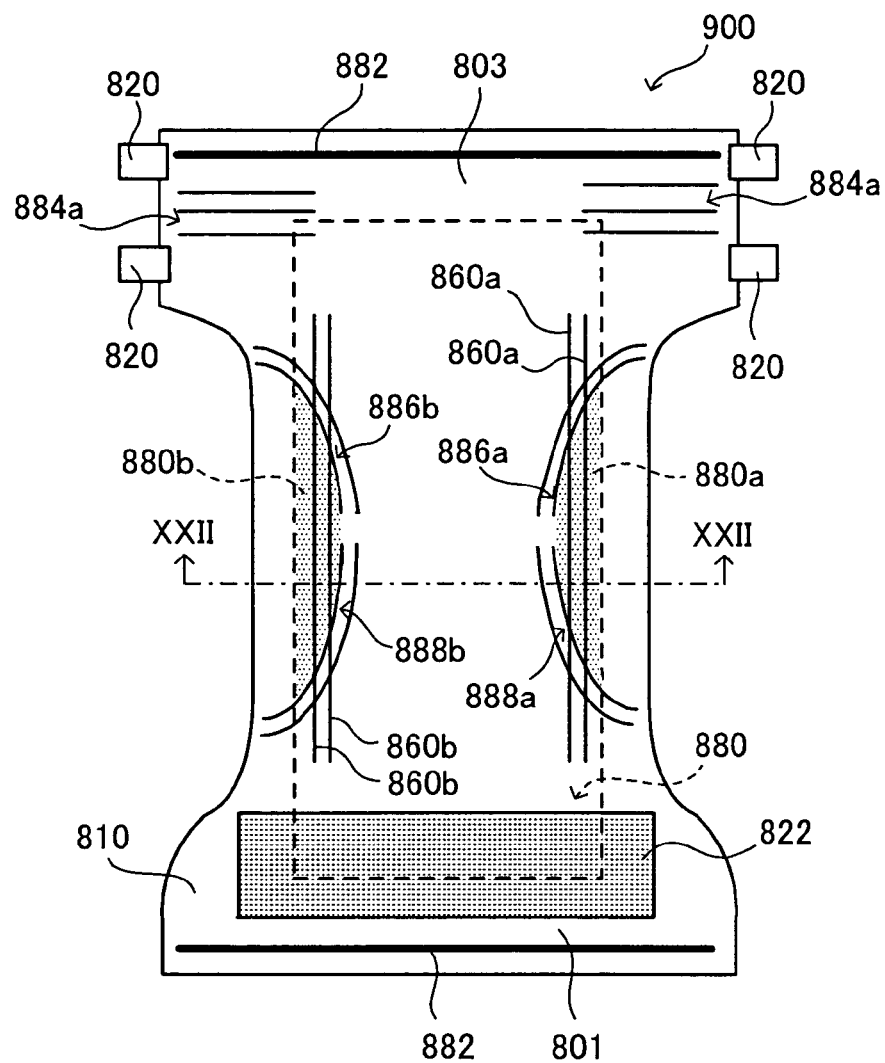
FIG. 22A is a plan view schematically showing the state when a pull-on type disposable diaper according to a fifth modified example according to an embodiment of the present invention is held in a strained state, and is seen from the side which becomes the external surface when worn.
FIG. 22B is a schematic diagram of a section along the line XXII—XXII shown in FIG. 22A.
Figure 22:
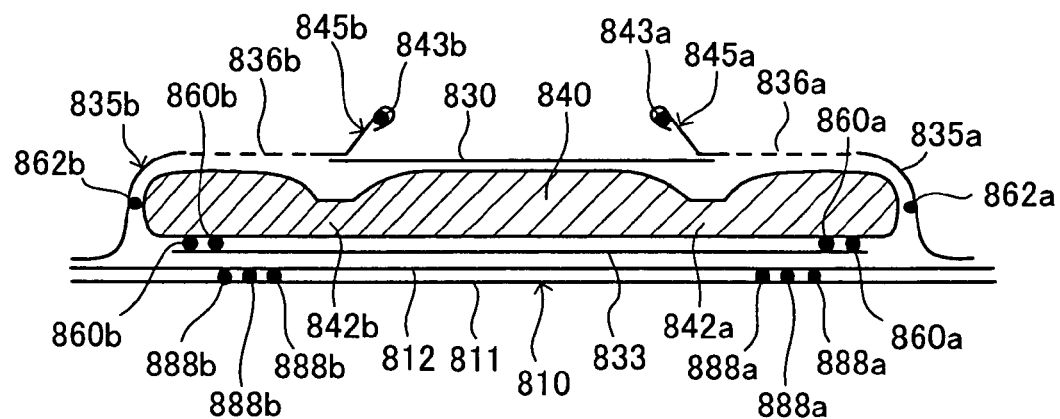

FIG. 22A schematically shows the state when a pull-on type disposable diaper 900 according to the fifth modified example is held in a strained state, and is seen from the side which becomes the external surface when worn, and FIG. 22B schematically shows a section of the pull-on type disposable diaper 900 along the line XXII—XXII shown in FIG. 22A.

The illustrated pull-on type disposable diaper 900 is considerably different from the pull-on type disposable diaper 100 in the first embodiment in that it is an expanding type disposable diaper (hereinafter, referred to as "expanding type disposable diaper 900"). The other configuration is the same as that of the pull-on type disposable diaper 500 in the first modified example. The constructional elements or areas shown in FIG. 22A or FIG. 22B having the same functions as those shown in FIG. 14 or FIG. 15 are denoted by the same reference symbols used in FIG. 14 or FIG. 15 added with 400, and the description thereof is omitted.

Reference symbol 820 in FIG. 22A or FIG. 22B denotes a fastening tape for connecting a front side portion 801 and a back side portion 803 at the time of using the expanding type disposable diaper 900, and reference symbol 822 denotes a sheet on which the respective fastening tapes 820 are fixed at the time of using the expanding type disposable diaper 900. In FIG. 22A, the respective elastic members are expressed by solid lines for the convenience sake.

The configuration of an absorbent article body 880 in the expanding type disposable diaper 900 is the same as that of the absorbent article body 480 in the pull-on type disposable diaper 500 in the first modified example. Therefore, the expanding type disposable diaper 900 exhibits the same technical effects as those of the pull-on type disposable diaper 500.

As described above, according to the present invention, there can be provided a pull-on type disposable diaper that can sufficiently absorb a large amount of body waste, and can easily improve the performance of preventing leakage from the crotch portion.

The present invention is not limited to the above-described embodiments or modified examples. The embodiments or modified examples are illustrations only, and any disposable diapers having substantially the same configuration as the technical idea described in the scope of claims of the present invention and similar working effects are included in the technical range of the present invention.

For example, the shape of the absorbent article body when the pull-on type disposable diaper is expanded and held in a strained state, and the shape of the absorbent article body when the expanding type disposable diaper is held in a strained state maybe an hour glass shape with the central part in the longitudinal direction being narrow, a trapezoidal shape, other than the rectangular shape as in the absorbent article bodies in the respective embodiments or respective modified examples.

It is also possible to define the external shape of the diaper by the top sheet and the back sheet constituting the absorbent article body, and in this case, the outer layer sheet can be omitted.

It will be obvious for those skilled in the art that various modifications, improvements and combinations other than those described above are possible.

What is claimed is:

1. A disposable diaper comprising a liquid-holding type absorbent article body in which an absorbent core is arranged between a liquid permeable top sheet and a liquid impermeable back sheet, in which a pair of right and left leg openings through which the legs pass at least at the time of wearing the disposable diaper is formed, and a plurality of leg portion elastic members is arranged around the respective leg openings in an extended state, wherein the leg portion elastic member includes at least one first leg portion elastic member provided in a front side portion which can be applied to the abdomen of a wearer so as to draw an arc along the leg openings, and at least one second leg portion elastic member provided in a back side portion which can be applied to the back of the wearer so as to draw an arc along the leg openings, the second leg portion elastic member being isolated from the first leg portion elastic member in a crotch portion which can be applied to the crotch of the wearer when worn, the minimum width of the absorbent article body in the crotch portion is within the range of from about 250 to 350 mm, and opposite side edges in the width direction of the absorbent article body in the crotch portion bend towards an external surface when worn, so that the respective opposite side edges in the width direction form leg flap absorbent articles which are capable of abutting against the inner part of the thigh of the wearer.

2. A disposable diaper according to claim 1, further comprising an outer layer sheet which defines the external shape of the diaper, wherein the absorbent article body is arranged on one face of the outer layer sheet, and the width of the absorbent article body is wider than the width of the outer layer sheet in at least a part of the crotch portion.

3. A disposable diaper according to claim 1, wherein the first leg portion elastic member provided along one of the pair of leg openings and the first leg portion elastic member provided along the other of the pair of leg openings are continuous in the crotch portion, and the second leg portion elastic member provided along one of the pair of leg openings and the second leg portion elastic member provided along the other of the pair of leg openings are continuous in the crotch portion.

4. A disposable diaper according to claim 1, wherein a gap formed between the first leg portion elastic member and the second leg portion elastic member in the crotch portion is within the range of from about 1% to 70% of the length in the longitudinal direction of the leg flap absorbent article.

5. A disposable diaper according to claim 1, wherein the length in the longitudinal direction of the leg flap absorbent article is within the range of from about ⅕ to ⅔ of the length in the longitudinal direction of the diaper.

6. A disposable diaper according to claim 1, wherein at least one leg flap elastic member is arranged along the longitudinal direction of the leg flap absorbent article on the external surface of the respective leg flap absorbent articles, and the extending stress of the respective leg flap elastic member is smaller than that of the first leg portion elastic member and the second leg portion elastic member.

7. A disposable diaper according to claim 1, wherein at least one leg flap side elastic member is arranged along the side edge, respectively at the opposite side edges of the absorbent article body in the crotch portion, and the extending stress of the respective leg flap side elastic member is smaller than that of the first leg portion elastic member and the second leg portion elastic member.

8. A disposable diaper according to claim 1, wherein at the respective opposite sides in the width direction of the absorbent article body, there are formed first liquid impermeable three-dimensional guards, liquid permeable side absorbing areas formed outside of the first three-dimensional guards in the width direction for enabling the body waste which has flowed over the first three-dimensional guards and penetrated into the leg flap absorbent articles, and liquid impermeable side areas formed outside of the side absorbing areas in the width direction for preventing the body waste absorbed by the absorbent article body from exuding from the side edges of the absorbent article body.

9. A disposable diaper according to claim 2, wherein when held in a strained state, a ratio a/b of the length "a" in the longitudinal direction of the leg opening with respect to the maximum width "b" of the leg opening, is not smaller than about 3.3, and the shortest distance from a point located innermost in the width direction at the side edge of the outer layer sheet in the crotch portion to the side edge of the absorbent article body is not longer than 40 mm.

10. A disposable diaper according to claim 1, comprising bending devices which assist bending of the opposite side edges in the width direction of the absorbent article body toward the external surface.

11. A disposable diaper according to claim 10, wherein the first leg portion elastic member and the second leg portion elastic member serve as the bending devices.

12. A disposable diaper according to claim 10, wherein the bending devices are embosses applied to the absorbent article body, isolated from the side edges in the width direction toward the inside of the absorbent article body.

13. A disposable diaper according to claim 10, wherein the bending devices are low-rigidity areas having relatively low rigidity, formed in the absorbent article body isolated from the side edges in the width direction toward the inside of the absorbent article body.

14. A disposable diaper according to claim 10, wherein the bending devices are low-rigidity areas, formed in the absorbent article body isolated from the side edges in the width direction toward the inside in the width direction of the absorbent article body, and the low-rigidity are formed by any of the following methods:

(i) tearing out a part of the absorbent article body;
(ii) making a part of the absorbent core have lower basis weight than that of other regions;
(iii) making a part of the absorbent core thinner than other regions.

* * * * *